United States Patent
Rousselle

(10) Patent No.: US 7,645,740 B2
(45) Date of Patent: Jan. 12, 2010

(54) PEPTIDE SEQUENCE FOUND IN LAMININ 5 FOR TREATING SKIN IMPAIRMENTS

(75) Inventor: Patricia Rousselle, Saint Genis Laval (FR)

(73) Assignee: Laboratoires d'Anjou Centre National de la Recherche Scientifique (CNRS), Paris (FR)

( * ) Notice: Subject to any disclaimer, the term of this patent is extended or adjusted under 35 U.S.C. 154(b) by 86 days.

(21) Appl. No.: 11/572,774

(22) PCT Filed: Jul. 29, 2005

(86) PCT No.: PCT/FR2005/001999

§ 371 (c)(1),
(2), (4) Date: Apr. 11, 2007

(87) PCT Pub. No.: WO2006/018551

PCT Pub. Date: Feb. 23, 2006

(65) Prior Publication Data

US 2008/0064641 A1   Mar. 13, 2008

(30) Foreign Application Priority Data

Jul. 29, 2004  (FR)  ................................... 04 08383

(51) Int. Cl.
*A61K 8/64*   (2006.01)
*A61K 38/10*  (2006.01)
*C07K 7/08*   (2006.01)

(52) U.S. Cl. .................. 514/14; 424/401; 530/327
(58) Field of Classification Search .................. None
See application file for complete search history.

(56) References Cited

U.S. PATENT DOCUMENTS 6,294,356 B1     9/2001  Jones et al.
2003/0175398 A1* 9/2003  Ogasawara et al. ......... 426/580

FOREIGN PATENT DOCUMENTS

WO     WO 00/66731 A2    11/2000

OTHER PUBLICATIONS

Boyce et al., "Cultivation, frozen storage, and clonal growth of normal human epidermal keratinocytes in serum-free media," J. Tissue Culture Methods, 1985, 9(2), 83-93.

* cited by examiner

*Primary Examiner*—Jeffrey E Russel
(74) *Attorney, Agent, or Firm*—Foley & Lardner LLP

(57) ABSTRACT

Peptide of sequence TALRIRATYGEY (SEQ ID NO: 1) present on the gamma 2 chain of Laminin 5, a pharmaceutical composition containing the peptide and to the use of the composition for treating various skin alterations. More particularly, the treatment of the alterations includes reinforcing the derma-epidermal junction and the cell-matrix and/or cell-cell adherence of epidermis and in promoting the repair of a cutaneous surface.

20 Claims, 20 Drawing Sheets

*FIG. 11A* (0%)
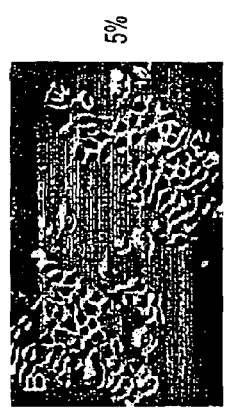
*FIG. 11B* (5%)
*FIG. 11C* (2.5%)
*FIG. 11D* (1.25%)
*FIG. 11E* (0.6%)
*FIG. 11F* (0.3%)

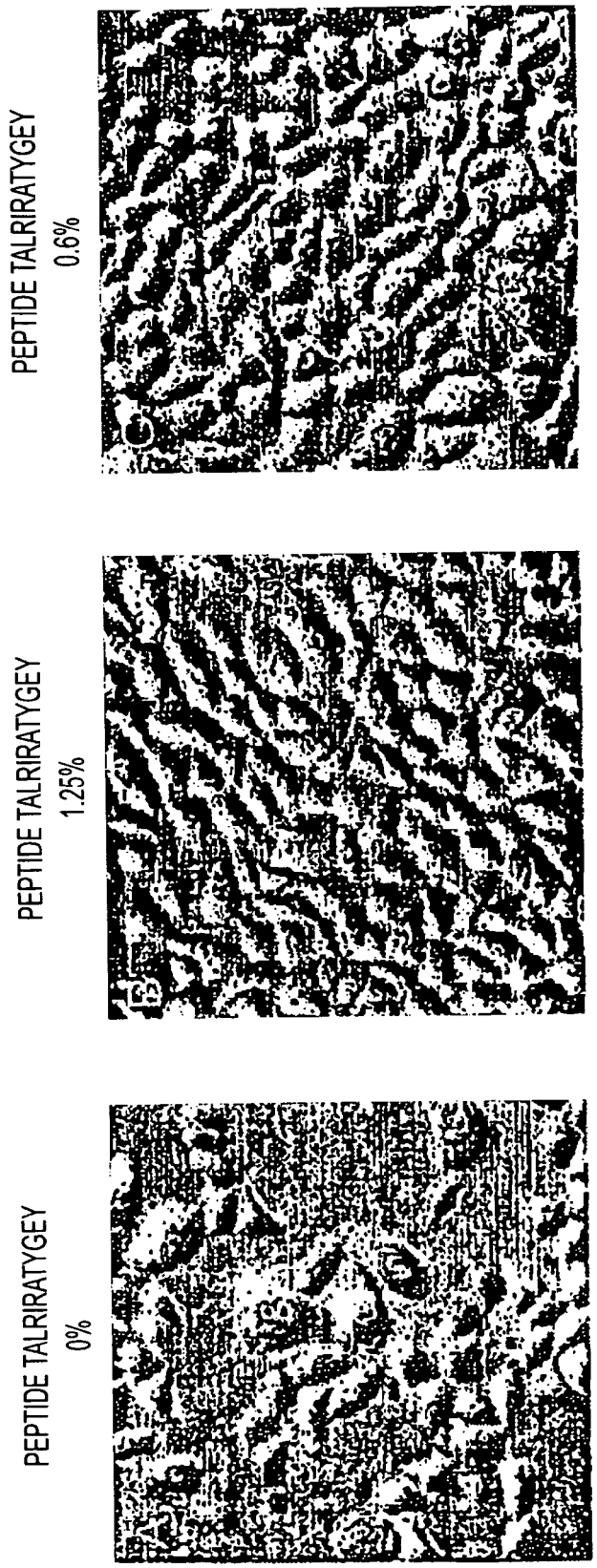

SUMMARY TABLE OF DOSES OF NON-IMMOBILIZED PEPTIDE USING THE
TECHNIQUE FOR DETERMINING AMINO ACID COMPOSITION (1ST SECTION)

| µg DEPOSITED /WELL | MEAN DEPOSITED /WELL | SUPERNATANT /WELL 1 | SUPERNATANT /WELL 2 | SUPERNATANT /WELL 3 | MEAN SUPERNATANTS | SD | % NON-IMMOBILIZED PEPTIDE | % IMMOBILIZED |
|---|---|---|---|---|---|---|---|---|
| ASSAY 1 | | | | | | | | |
| 5.04µg | | | | | | | | |
| 5.34µg | 5.19µg | 4.77µg | 5.40µg | 5.35µg | 6.17µg | 0.35µg | 97%* | * |
| ASSAY 2 | | | | | | | | |
| 3.47µg | | | | | | | | |
| 3.64µg | 3.55µg | 3.11µg | 3.33µg | nd | 3.22µg | 0.15µg | 90% | 10% |
| ASSAY 3 | | | | | | | | |
| 2.49µg | | | | | | | | |
| 2.63µg | 2.56µg | 2.23µg | 2.44µg | 2.41µg | 2.36µg | 0.11µg | 92% | 8% |
| ASSAY 4 | | | | | | | | |
| 1.28µg | | | | | | | | |
| 1.20µg | 1.23µg | 1.12µg | 1.11µg | 1.08µg | 1.10µg | 0.018µg | 90% | 10% |
| ASSAY 5 | | | | | | | | |
| 0.65µg | | | | | | | | |
| 0.82µg | 0.73µg | 0.64µg | 0.61µg | 0.73µg | 0.66µg | 0.00µg | 90% | 10% | nd: NOT IDENTIFIED
*: THIS VALUE CANNOT BE TAKEN INTO ACCOUNT SINCE THE QUANTITIES OF PEPTIDE FOUND IN THE SUPERNATANT IN BOTH CASES WERE HIGHER THAN THOSE PRESENT IN THE STARTING SOLUTION.

FIG. 17

SUMMARY TABLE OF DOSES OF NON-IMMOBILIZED
PEPTIDE USING THE TECHNIQUE FOR DETERMINING AMINO
ACID COMPOSITION (2ND SECTION)

| ug DEPOSITED /WELL | MEAN | SUPERNATANT WELL 1 | SUPERNATANT WELL 2 | SUPERNATANT WELL 3 | SUPERNATANT WELL 4 | SUPERNATANT WELL 5 |
|---|---|---|---|---|---|---|
| ASSAY 1 | | | | | | |
| 2.46µg | 2.44µg | 2.19µg | 2.23µg | 2.04µg | 2.28µg | 2.34µg |
| 2.42µg | | | | | | |
| ASSAY 2 | | | | | | |
| 1.08µg | 1.09µg | 1.00µg | 0.93µg | 1.03µg | 0.98µg | 1.07µg |
| 1.09µg | | | | | | |

| | MEAN SUPERNATANTS | SD | % NON-IMMOBILIZED PEPTIDE | % IMMOBILIZED |
|---|---|---|---|---|
| ASSAY 1 | 2.212µg | 0.11µg | 90.65% | 9% |
| ASSAY 2 | 1.002µg | 0.05µg | 92% | 8% |

FIG. 18

PEPTIDE SEQUENCE FOUND IN LAMININ 5 FOR TREATING SKIN IMPAIRMENTS

CROSS REFERENCE TO RELATED APPLICATIONS

This application is a National Stage application of PCT/FR2005/01999, filed Jul. 29, 2005, which claims priority from French patent application FR 0408383, filed Jul. 29, 2004.

This invention relates to a novel peptide, a pharmaceutical composition containing said peptide and the use of such a composition in the treatment of skin impairing of various origins.

More particularly, the treatment of said impairing consists in reinforcing the dermo-epidermal junction, cell-cell adhesion and/or cell-matrix adhesion in the epidermis and enhancing repair of the cutaneous surface.

The invention further relates to a cosmetic treatment process comprised of the application of this pharmaceutical composition to the skin.

The most common and most natural skin impairing are simply due to the aging process.

Skin aging is a complex phenomenon triggered by several intrinsic factors (genetic factors) and extrinsic factors (such as sun, diet, exposure to cigarette smoked, etc.) Clinically, this is seen in the form of the appearance of wrinkles and crow's-feet, loss of skin elasticity, loosening of the cutaneous and subcutaneous tissue, as well as less efficient healing of wounds.

Many research approaches have been put forward to fight skin aging. These include protection against the external environment (sun, pollution, etc), activation of cell regeneration and strengthening the extracellular matrix (collagen and elastin). Recent studies have revealed the importance of the adhesion of cells to each other, on the one hand, and the adhesion of cells to the extracellular matrix, on the other, in the course of skin aging. Consequently, it is important to reinforce these factors in order to prevent and perhaps even treat sagging skin.

Dermatological studies, which have recently turned to the use of peptides (sequences derived from alpha-MSH, some neuropeptides, RGD peptide) in skin biology, are being directed towards research into peptides with a high level of activity in the skin.

The cosmetic industry is also constantly awaiting a new peptide capable of increasing the adhesion of cells to the extracellular matrix and/or the adhesion of cells to each other.

Interactions between cells and the extracellular matrix (ECM) play an important role in the control of cell behaviour. This takes the form of specific interactions between matrix molecules and cells in the transmembrane receptors, mainly the integrins whose intracellular space is linked to cytoskeleton constituents. This allows the matrix to ensure the transmission of intracellular signals which modulate the adhesion, migration, proliferation, differentiation and apoptosis of epidermal cells. This control of cell behaviour is crucial during development as well as in the course of tissue modification.

Depending on the constituent molecules and resulting organization, there are several types of ECM, with the basal layers without a doubt being the most specialized. The latter consist of a continuous, fine protein trellis on which the organism's various cell layers rest. They were for many years defined as discrete morphological structures whose function was limited to partitioning tissue compartments. It is only in the past 15 years that significant advances have been made in investigating their molecular composition and function, in spite of their limited numbers and low solubility. It appears that these structures play a fundamental role in the control of cell behaviour, in terms of both embryo development and maintaining the intactness of differentiated cell phenotypes.

Skin consists of the following structures:
  a coating epithelium: the epidermis,
  conjunctive tissue: the dermis (thick layer determining skin morphology and containing blood and lymph vessels and nerves) and
  adipose tissue: the hypodermis.

The dermis and epidermis are connected by a unique and complex structure, the dermo-epidermal junction (DEJ) or epidermal basal layer. Anatomically, this corresponds to the area between the basal cells of the epidermis and the outermost layers of the dermis. This is an adhesion zone which partitions the polarized epithelium and subjacent stroma and provides support and cohesion for adjacent cells. The DEJ, consisting exclusively of extracellular matrix, plays two roles:

1) mechanical role: its unique molecular structure confers great mechanical stability on it, providing the epidermis with a solid anchorage point,
2) biological role: DEJ proteins are closely linked to the basal cells of the epidermis and transmit important morphogenetic information through the integrin receptors.

The DEJ is also a diffusion filter for nutritional and metabolic factors. It therefore allows biological information to be transmitted.

In the course of skin aging, the DEJ becomes flatter and gradually loses its characteristic undulations which considerably reduces the epidermis-dermis interface. In addition, the molecular networks become disorganized, the protein framework becomes more fragile and the adhesion of basal keratinocytes is reduced.

Consequently, mechanical (support) and biological functions (exchange of information and molecules) in the DEJ are altered.

In the case of skin injuries, the DEJ is damaged and its constituent molecules are broken down by specific enzymes. Under favourable conditions, epidermal re-epithelization begins a few hours after injury. Once the epithelium has covered the wound bed, DEJ proteins reappear in a sequential and ordered manner.

With skin aging, each of these steps takes place more slowly. In particular, it has been found that there is a decrease in the expression of matrix proteins and membrane receptors which might be a major cause in the delay observed in the DEJ reconstitution process and the extreme fragility of scar tissue in elderly people.

Laminin 5 (LN-5) is a protein specifically expressed in the basal layers of specialized squamous and transitional epithelia such as the cutaneous dermo-epidermal junction. LN-5 results from the heterotrimeric assembly of alpha 3, beta 3 and gamma 2 subunits and is synthesized exclusively by epithelial cells in the form of a 460 kDa precursor. Under physiological conditions, each of the alpha 3 and gamma 2 subunits undergoes post-translational extracellular cleaving of the terminal carboxy and amino groups, leading to the mature tissue form. Recent studies suggest that the entirety of the gamma 2 precursor chain is necessary for secretion and incorporation of LN-5 into ECM.

The key role of LN-5 is emphasized by the existence of hereditary or acquired disorders resulting in synthesis and/or expression abnormalities of one of the constituent subunits. These disorders, called junctional bullous epidermolyses, lead in particular to fragility of the cutaneous dermo-epidermal junction characterised by the spontaneous formation of epidermal bulla. LN-5 therefore plays a crucial and irreplaceable role in epithelio-mesenchymatous cohesion. LN-5 carries formative biological signals because these allow the adhesion of adjacent epithelial cells through the intermediary of the integrins and result in the assembly of stable adhesion structures, the hemidesmosomes.

International patent application WO 00/66731 in the name of Biostatum describes the production of whole LN-5 in recombinant form in eukaryote cells (L5r) and documents its activity in improving scar formation and cell proliferation and adhesion.

The applicant has surprisingly and unexpectedly found that an effective amount of a peptide sequence TALRIRATYGEY (SEQ ID No. 1), a sequence present on the gamma 2 chain of LN-5, specifically leads to the adhesion of epidermal keratinocytes and other epithelial cells. This peptide not only allows increased adhesion of cells to the ECM but also increases the adhesion of cells to each other. With its small size and great stability, this peptide has all the characteristics needed for it to cross the epidermis and reach its target, the DEJ, and thus interact with the basal keratinocytes and transmit signals to trigger adhesion. A fragment of LN-5, it appears to restore its deficient or lacking native homologue and appears to have immediate biological activity in triggering the adhesion and restoration of mechanical properties to the DEJ. Its manufacturing process by chemical synthesis is straightforward and applicable at the industrial scale. It does not require cell cultures of animal origin nor any growth factors and/or serums or serum derivatives. As a result of its small size, it would not be or would only slightly be the target of specific and/or non-specific proteolytic degradation.

A first object of the invention is thus a peptide with the following sequence: TALRIRATYGEY (SEQ ID No. 1).

This invention also covers other peptides resulting from one or more modifications to SEQ ID No. 1 such as the addition, suppression or substitution of one or more amino acids, preferably as indicated in table 1, and/or oligomerisation, cyclisation or folding up of SEQ ID No. 1, it being given that these modifications in no way diminish the adhesive activity of the reference peptide and might even improve it.

TABLE 1

| Amino acid position | SEQ ID No. 1 | Other peptides according to the invention resulting from one or more of the following substances |
|---|---|---|
| 1 | T | X* |
| 2 | A | X* |
| 3 | L | L, M, I, V, F, E or R |
| 4 | R | R, N, E, Q, H, K or Y |
| 5 | I | I, M, L, V, F, T or K |
| 6 | R | R, N, E, Q, H, K or T |
| 7 | A | A, C, S, G, V or D |
| 8 | T | T, S P, G, N, D, E, Q, H or K |
| 9 | Y | Y, H, F, W, D, I or Q |
| 10 | G | G, S, T, A or N |
| 11 | E | X* |
| 12 | Y | X* |

*X being any amino acid.

More particularly, the addition or removal or one or more amino acids can be carried out on the terminal carboxy and/or amino side of said peptide. Another objective of the invention is any analogue or derivative resulting from the grafting of a group of interest (natural or synthetic molecules, proteins and/or sugars) to said peptide. Another objective is any dermatologically active fragment of the peptide of the invention, modified or not.

The peptide according to this invention is characterised in that it is obtained by chemical synthesis.

Another objective of the invention is a pharmaceutical composition characterised in that it contains at least one peptide according to this invention.

The term "pharmaceutical composition" refers to any dermatological composition suitable for use for cosmetic and/or therapeutic purposes.

According to one advantageous embodiment of the invention, the above-mentioned peptide undergoes preliminary solubisation in one or more cosmetically or pharmaceutically acceptable solvents such as water, propylene glycol, butylene glycol, ethoxylated or propoxylated diglycols, ethanol, propanol or isopropanol.

According to one advantageous embodiment of the invention, the above-mentioned peptide undergoes preliminary solubilisation in a pharmaceutical vector such as liposomes or is adsorbed onto powdered organic polymers, mineral supports such as talc and bentonite, and more generally in or fixed onto any acceptable pharmaceutical vector.

The pharmaceutical compositions of this invention contain 0.00002 to 5%, preferably 0.00005 to 0.1%, even more preferably 0.0001 to 0.001% by weight of the peptide of the invention, at least one pharmaceutically acceptable excipient known to the man skilled in the art such as solvents, thickeners, diluents, surfactants, anti-oxidants, dyes, preservatives and/or fragrances, depending on the final formulation of the composition of the invention.

The inventors have demonstrated that quantities, even small ones (in the order of 0.00002% by weight of the peptide of the invention in a pharmaceutical or cosmetic composition), are sufficient to obtain the required activity. This invention describes maximum quantities of 5% by weight of the peptide of the invention in a pharmaceutical or cosmetic composition) for economic reasons. However, the professional can envisage using quantities in excess of 5% and adapt the concentration, if need be, to obtain at least an equal effect as a function of cost and purity of the peptide according to the invention.

More particularly, the composition of this invention also includes at least one dermatologically active ingredient acting on the skin to reinforce the dermo-epidermal junction, cell-matrix adhesion and/or cell-cell adhesion or in a different way, depending on the type of agent(s) used, such as a hydrating agent, relipidifying agent, moisturizing agent, exfoliant agent, keratolytic agent, anti-oxidant agent, soothing agent, softening agent, sedative agent, cleansing agent, make-up removing agent, toning agent, antibacterial agent, antiseptic agent, antiseborrhoeic agent, decongestant agent, revitalizing agent, cell renewal activating agent or one or more sun filters.

Preferably, this composition is intended for topical use.

The compositions of the invention must be in a dermatologically acceptable form, in other words compatible with skin, body and/or head hair. These compositions can be in the form of creams, milks, oil-in-water emulsions, water-in-oil emulsions, multiple emulsions, solutions, suspensions, aqueous gels, oily gels, hydroalcoholic gels, lotions, sticks or powders, adapted to application to the skin, mucous membranes and, in particular, the lips and/or hair.

Potential additional compositions, active or not, can be added to the composition of the invention and the man skilled in the art will choose them such that their addition does not alter the advantageous properties of said composition.

Another object of the invention, is the use of a peptide according to this invention for the preparation of a pharmaceutical composition intended for reinforcement of the dermo-epidermal junction, cell-matrix attachment and cell-cell adhesion in the epidermis and thus to promote epidermal repair.

As indicated earlier, the most commonly observed impairing to the epidermis and DEJ result from skin aging. However, other skin impairing can occur independently of aging and can, for example, be triggered by certain dermatological disorders. Examples of this include eczema, psoriasis, pruritus, irritative dermatitis, heliodermis, keratosis, mycosis, ichthyosis. In addition to the specific symptoms of each of these disorders, skin undergoes impairing which this invention proposes to remedy as a therapeutic complement. It is clear that this invention does not aim to treat such disorders but rather to restore damaged DEJ and cell adhesion associated with these disorders.

This invention therefore allows the repair, regeneration and/or restructuring of skin.

Skin can also be made fragile by cosmetic or therapeutic treatment which, while treating the disorder, gives rise to side effects to the skin which need to be treated independently of the disorder itself. This is notably the case with acne treatment, treatment by puvatherapy, surgery (dermatological or other), laser treatment of the skin, dermabrasion, peeling or cancer treatment by radiotherapy.

Finally, the composition of the invention is also intended for the curative and preventive treatment not only of skin aging, as shown above, such as wrinkles, loose skin, loss of elasticity and healing but also for the curative or preventive treatment of senile xerosis, changes to the skin's pigmentation system, reduced skin vascularisation, impairing to skin appendages such as nails, skin texture irregularities and cutaneous atrophy.

The above-mentioned disorders, skin fragilisation and various treatments lead to skin impairing such as decreased epidermal adhesion and epidermal cohesion or poorer restructuring of the cutaneous surface.

Finally, the invention relates to a cosmetic treatment procedure for the skin whereby a cosmetic composition containing at least one peptide according to the invention is applied to the skin. Said cosmetic composition according to the invention contains 0.00002 to 5%, preferably 0.00005 to 0.1%, even more preferably 0.0001 to 0.001% by weight of the peptide of the invention and at least one pharmaceutically acceptable excipient.

According to the invention, said cosmetic composition can also include at least one other cosmetically active ingredient.

According to the invention, said cosmetic composition is the form of a cream, milk, oil-in-water emulsion, water-in-oil emulsion, multiple emulsion, solution, suspension, aqueous gel, oily gel, hydroalcoholic gel, lotion, stick or powder, adapted to application to the skin, mucous membranes and, in particular, the lips and/or hair.

Other advantages and characteristics of the invention will become apparent on reading the examples illustrating the invention in a non-limiting manner.

Dose-dependent cell adhesion of cell line HBL100 to various peptides 1, 2 and 3. The peptides were immobilized in 96-well plates at the concentrations given on the abscissa. $8\times10^4$ cells were deposited in each well and plates were incubated at 37° C. for 1 hour. After washing, attached cells were fixed and cell adhesion was measured as described in the methodology section.

Cells were observed by phase contrast microscopy then photographed. Bar=50 μm.

Figure 2A:
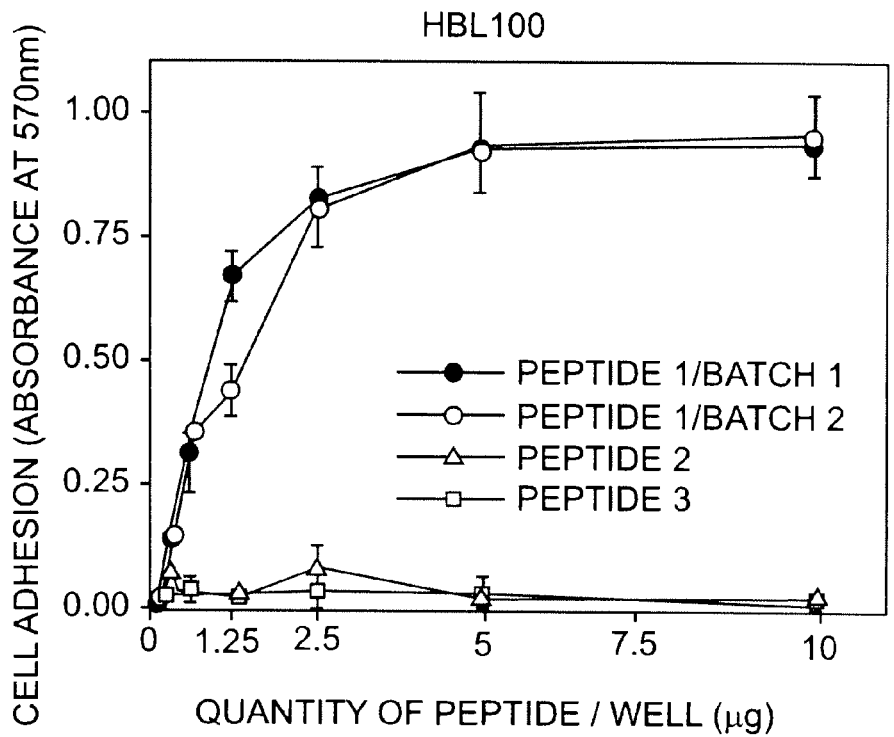
FIG. 2: Cell adhesion of HBL1000 to peptides 1, 2 and 3

FIG. 2A is a graph of cell adhesion as a function of peptide quantity for cell line HBL100.

Figure 2B:
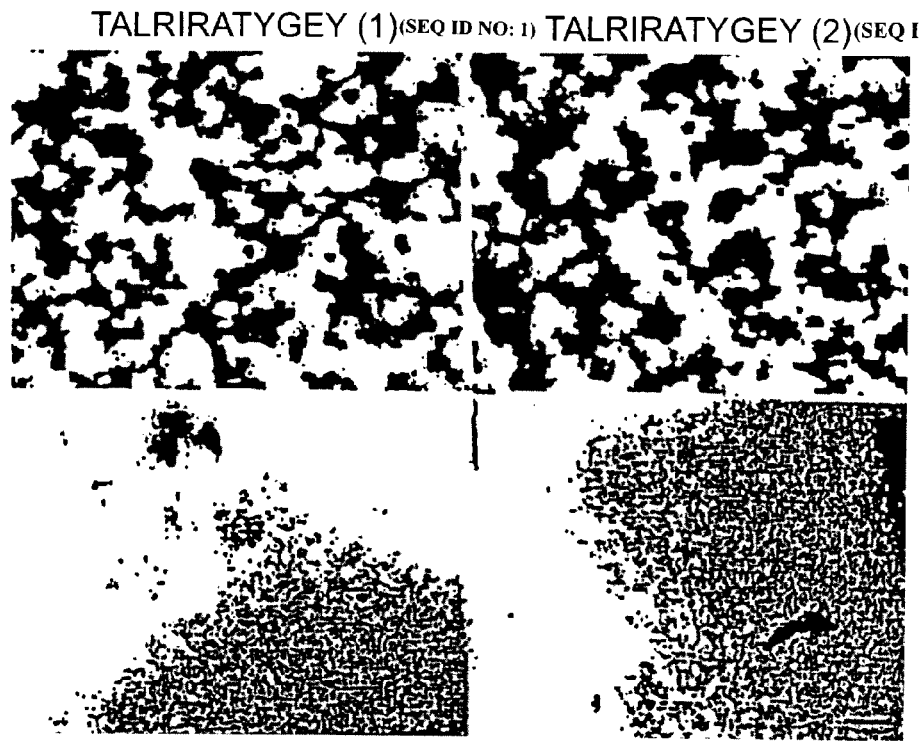

FIG. 2B is the corresponding photographs.

FIG. 3: Cell adhesion of HT1080 to peptides 1, 2 and 3

Dose-dependent cell adhesion of cell line HT1080 to various peptides 1, 2 and 3. The peptides were immobilized in 96-well plates at the concentrations given on the abscissa. $8\times10^4$ cells were deposited in each well and plates were incubated at 37° C. for 1 hour. After washing, attached cells were fixed and cell adhesion was measured as described in the methodology section.

Cells were observed by phase contrast microscopy then photographed. Bar=50 μm.

Figure 3A:
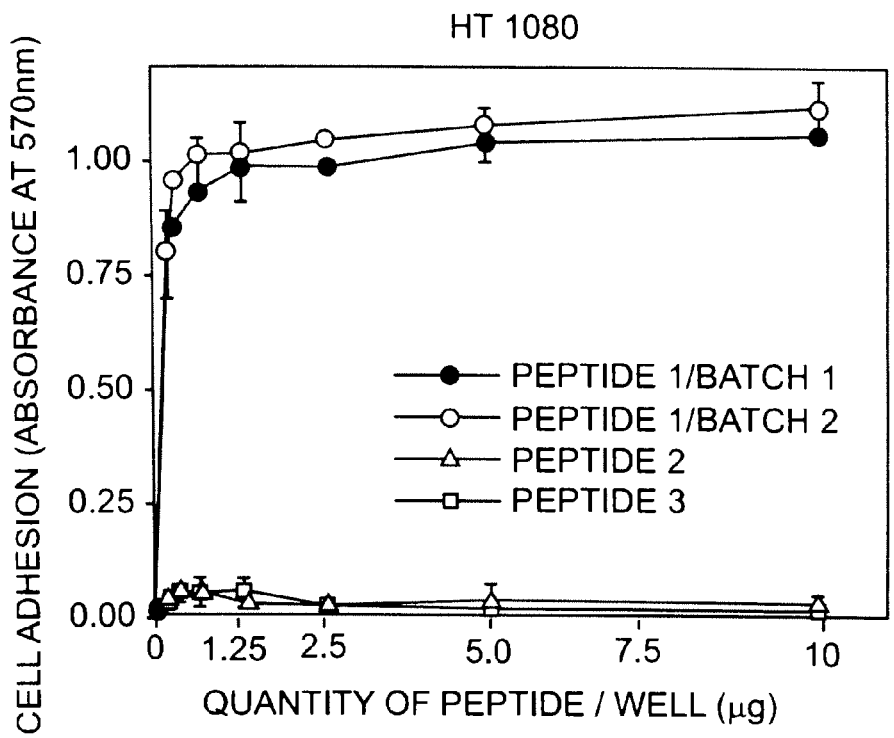

FIG. 3A is a graph of cell adhesion as a function of peptide quantity for cell line HT1080.

Figure 3B:
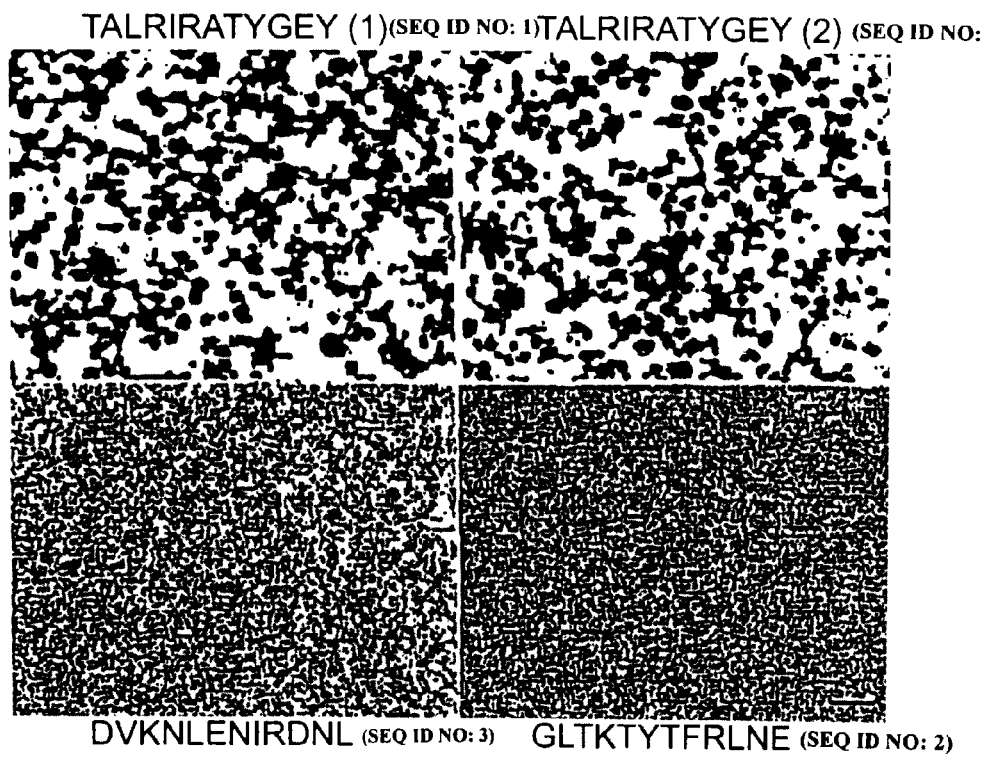

FIG. 3B is the corresponding photographs.

FIG. 4: Cell adhesion of A431 to peptides 1, 2 and 3

Dose-dependent cell adhesion of cell line A431 to various peptides 1, 2 and 3. The peptides were immobilized in 96-well plates at the concentrations given on the abscissa. $8\times10^4$ cells were deposited in each well and plates were incubated at 37° C. for 1 hour. After washing, attached cells were fixed and cell adhesion was measured as described in the methodology section.

Cells were observed by phase contrast microscopy then photographed. Bar=50 μm.

Figure 4A:
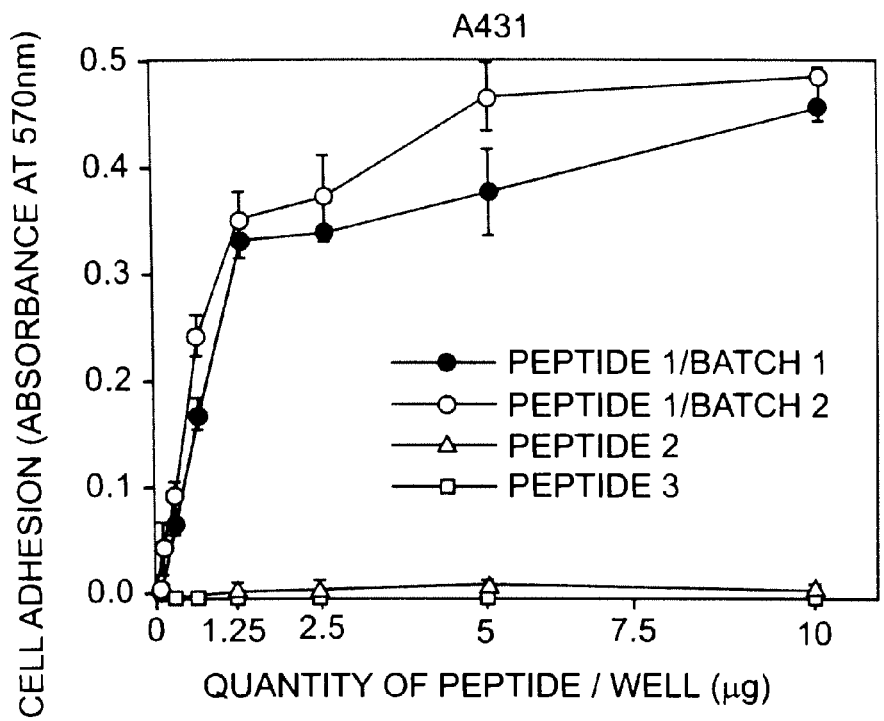

FIG. 4A is a graph of cell adhesion as a function of peptide quantity for cell line A431.

Figure 4B:
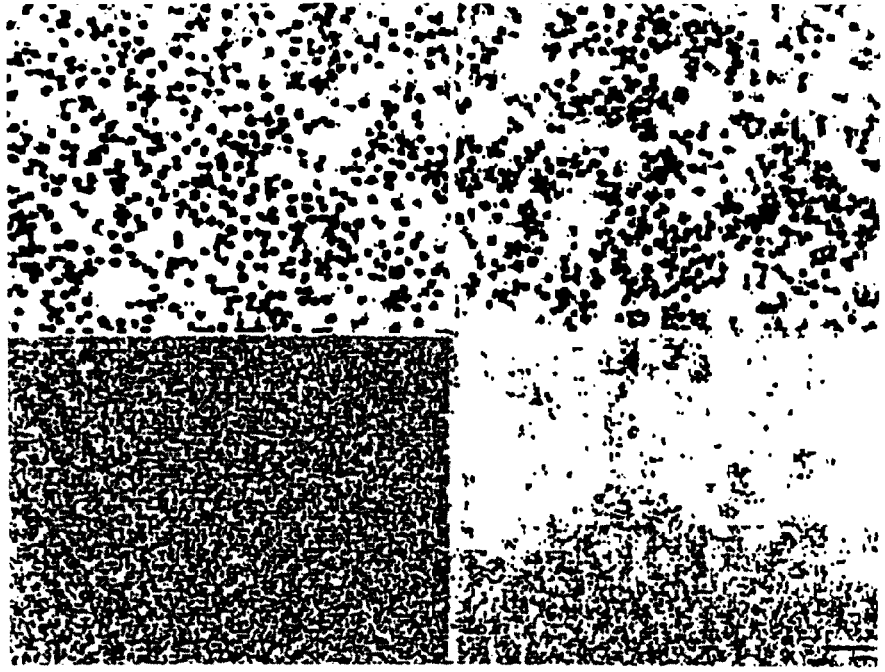

FIG. 4B is the corresponding photographs.

FIG. 5: Cell adhesion of normal human keratinocytes to peptides 1, 2 and 3

Dose-dependent cell adhesion of normal human keratinocytes to various peptides 1, 2 and 3. The peptides were immobilized in 96-well plates at the concentrations given on the abscissa. $10^5$ cells were deposited in each well and plates were incubated at 37° C. for 1 hour. After washing, attached cells were fixed and cell adhesion was measured as described in the methodology section.

Cells were observed by phase contrast microscopy then photographed. Bar=50 μm.

Figure 5A:
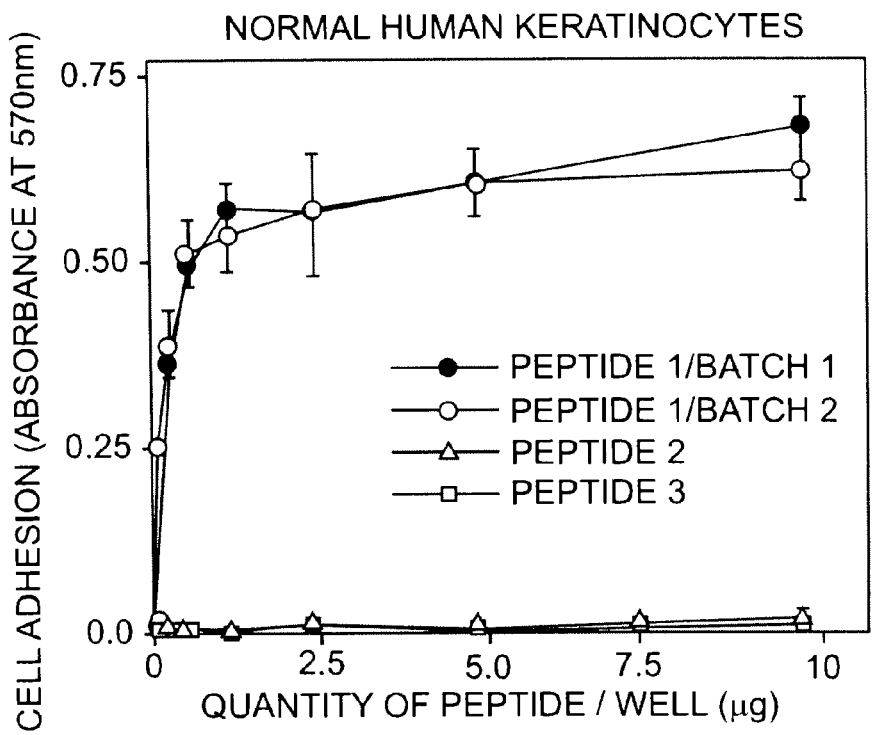

FIG. 5A is a graph of cell adhesion as a function of peptide quantity for normal human keratinocytes.

Figure 5B:
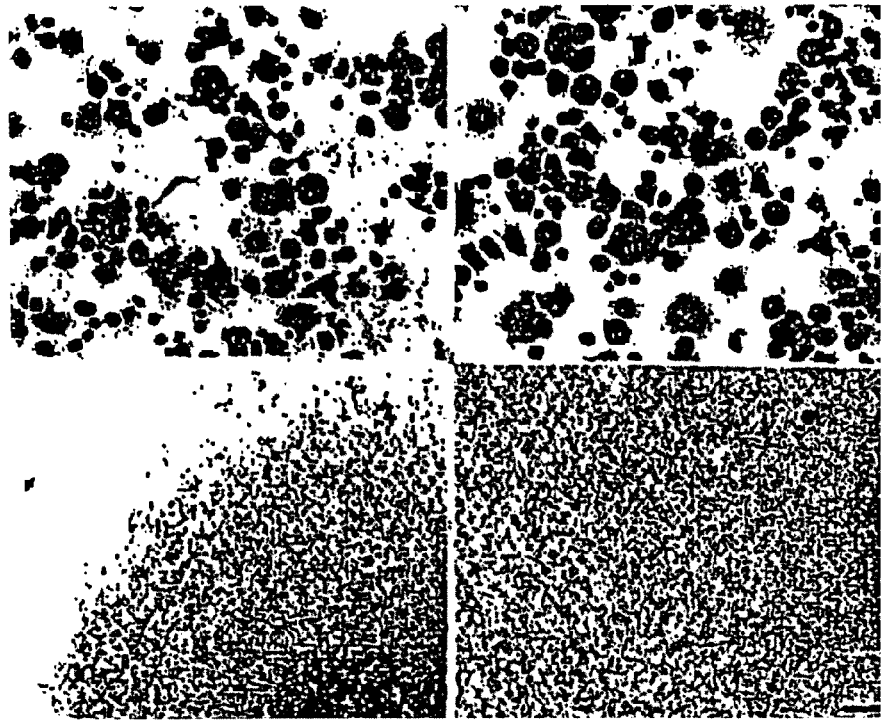

FIG. 5B is the corresponding photographs.

FIG. 6: Cell adhesion of NHK-young versus NHK-old to peptide TALRIRATYGEY (SEQ ID No. 1)

Dose-dependent cell adhesion of NHK-10 years versus NHK-71 years (A) and NHK-11 years versus NHK-60 years (B) peptides TALRIRATYHEY. The peptides were immobilized in 96-well plates at the concentrations given on the abscissa. $3.5\times10^4$ (A) cells and $4.3\times10^4$ (B) cells were deposited in each well and plates were incubated at 37° C. for 1 hour. After washing, attached cells were fixed and cell adhesion was measured as described in the methodology section (C). Cells were observed by phase contrast microscopy then photographed. Bar=50 μm.

Figure 6A:
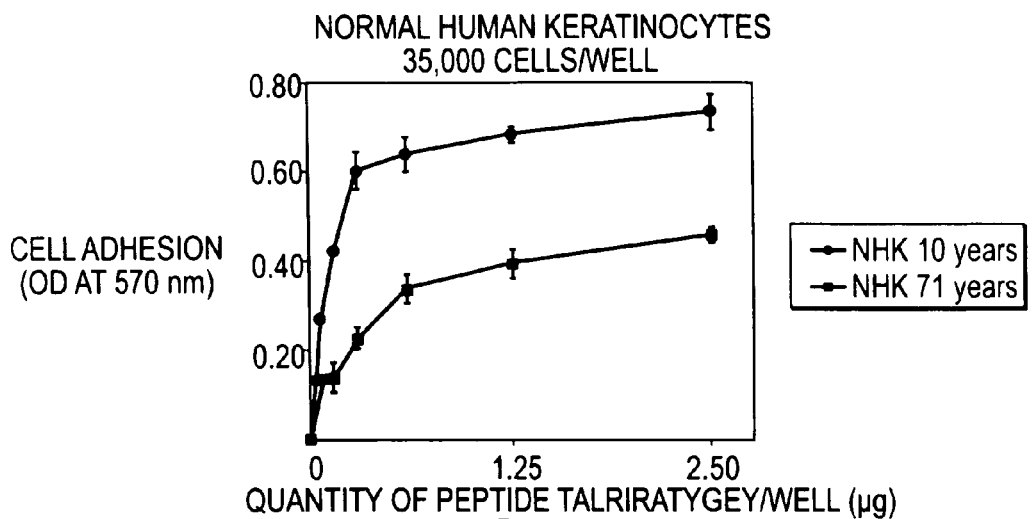
Figure 6B:
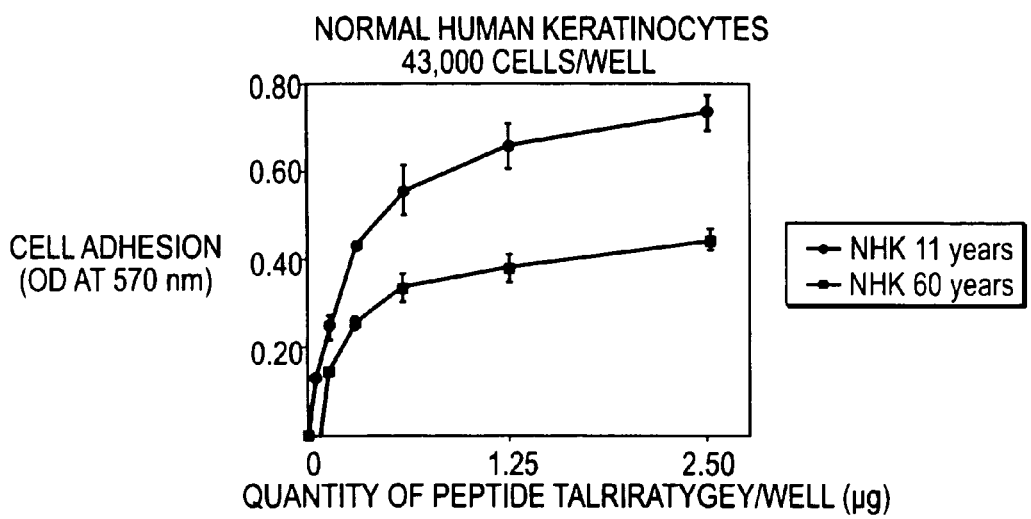

FIGS. 6A and 6B are corresponding graphs.

Figure 6C:
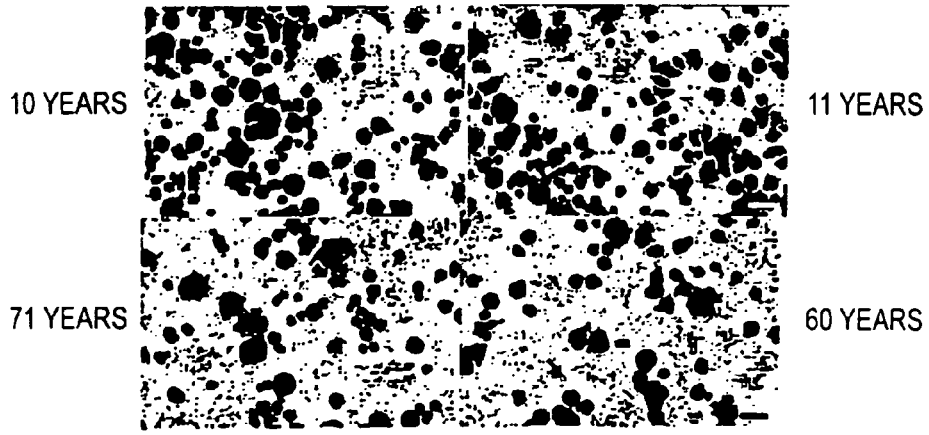

FIG. 6C is the corresponding photographs.

FIG. 7: Effect of peptide TALRIRATYGEY (SEQ ID No. 1) on the proliferation of HT1080 and HBL100 cells HT1080 cells (A) and HBL100 cells (B) were seeded in 96-well plates at a rate of 10,000 cells per well. After 24 hours, the culture medium was removed and replaced with serum-free medium containing the peptide quantities given in the graphs and reagent XTT. The plates were then placed in the incubator at 37° C. and absorbance readings were taken at 1 h, 2 h, 3 h, 4 h and 5 h. Peptide-free controls were carried out on the same plate.

Figure 7B:
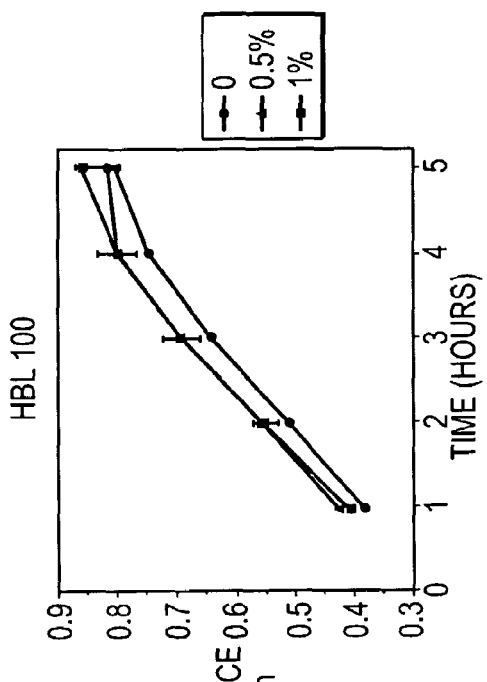
Figure 7A:
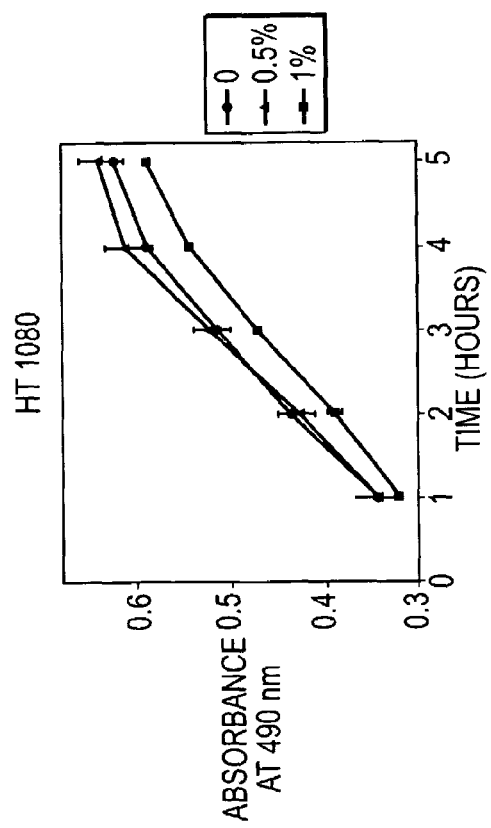

FIGS. 7A and 7B are corresponding graphs and Tables.

Figure 8:
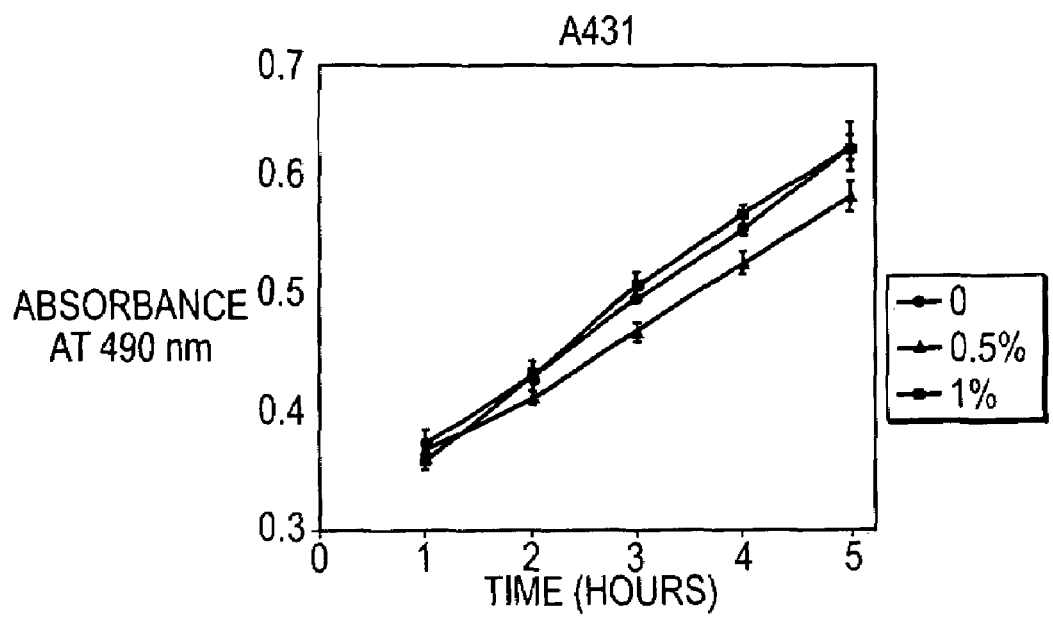

FIG. 8: Effect of peptide TALRIRATYGEY (SEQ ID No. 1) on the proliferation of A431 cells A431 cells were seeded in 96-well plates at a rate of 10,000 cells per well. After 24 hours, the culture medium was removed and replaced with serum-free medium containing the peptide quantities given in the graphs and reagent XTT. The plates were then placed in the incubator at 37° C. and absorbance readings were taken at 1 h, 2 h, 3 h, 4 h and 5 h. Peptide-free controls were carried out on the same plate.

Figure 9:
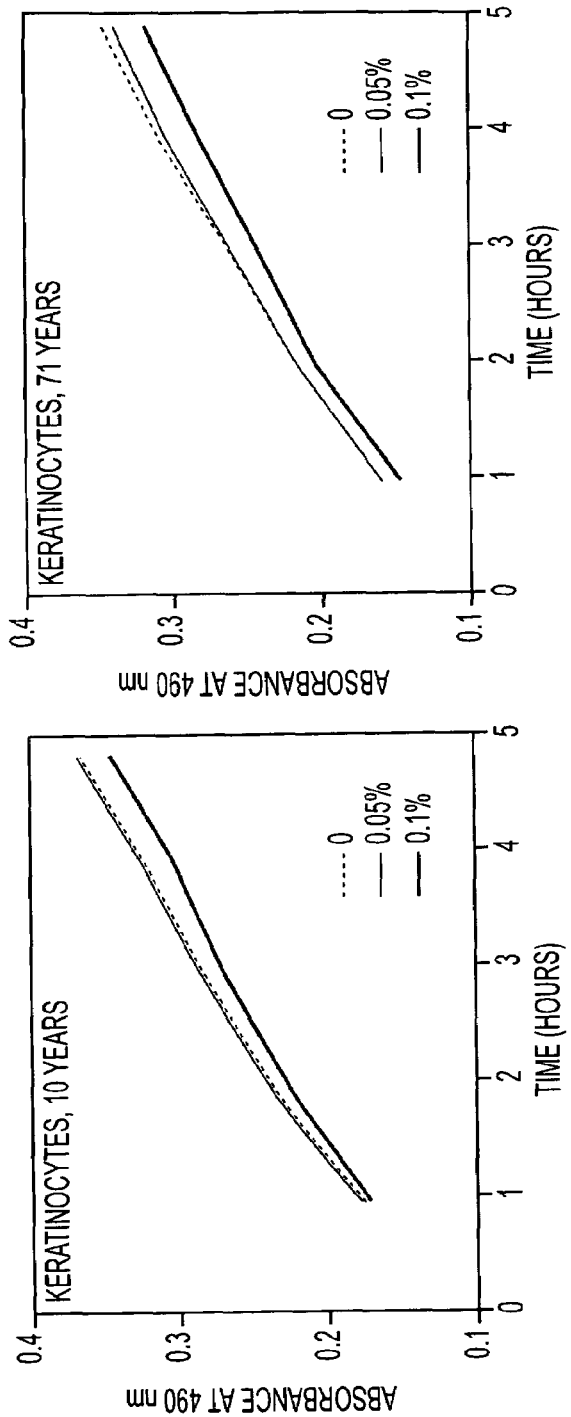

FIG. 9: Effect of peptide TALRIRATYGEY (SEQ ID No. 1) on the proliferation of NHK-young and NHK-old NHK-10 years and NHK-71 years were seeded in 96-well plates at a rate of 10,000 cells per well. After 24 hours, the culture medium was removed and replaced with serum-free medium containing the peptide quantities given in the graphs and reagent XTT. The plates were then placed in the incubator at 37° C. and absorbance readings were taken at 1 h, 2 h, 3 h, 4 h and 5 h. Peptide-free controls were carried out on the same plate.

Figure 10:
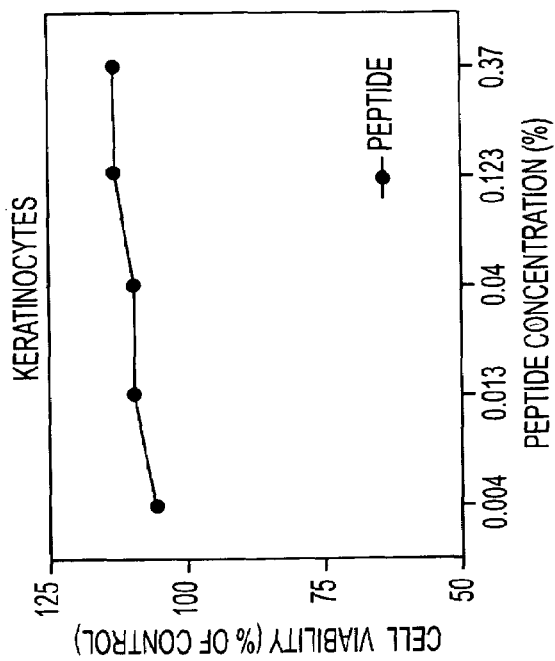

FIG. 10: Effect of peptide TALRIRATYGEY (SEQ ID No. 1) on the proliferation of NHKs NHKs were seeded in 96-well plates at a rate of 10,000 cells per well. After 24 hours, the culture medium was removed and replaced with KBM-2 medium containing the peptide quantities indicated. After 24 hours of contact at 37° C., the medium was removed and replaced with reagent XTT. The plates were then placed in the incubator at 37° C. and absorbance readings were taken 3 h. Peptide-free controls were carried out on the same plate.

FIG. 11: Effect of peptide TALRJRATYGEY (SEQ ID No. 1) on the proliferation of NHKs NHKs were seeded in 12-well plates at a rate of 5,000 cells per well. After 24 hours, the culture medium was removed and replaced with new medium containing 5%, 2.5%, 1.25%, 0.6% and 0.3% peptide (B—F). A peptide-free control was carried. The plates were then placed in the incubator at 37° C. for 48 hours. Observations were made with an Axiovert 40 Zeiss microscope. Bar=50 µm FIG. 11A is the resulting photograph for the control.

FIGS. 11B, 11C, 11D, 11E and 11F are the resulting photographs for 5%, 2.5%, 1.25%, 0.6% and 0.3% peptide, respectively.

FIG. 12: Effect of peptide TALRIRATYGEY (SEQ ID No. 1) on the behaviour of NHKs

Observation at higher magnification of the cell colonies described in FIG. 6 using an Axiovert 40 Zeiss microscope equipped with a PlasDisc interferential block. Bar=50 µm

FIG. 13

(A) Diagrammatic representation of laminin 5 and collagen IV in the dermo-epidermal junction (DEJ). (B) Dose-dependent cell adhesion of NHKS to laminin 5 and collagen IV. laminin 5 and collagen IV were fixed to 96-well plates in the quantities given on the abscissa. $5 \times 10^4$ NHKs were deposited in each well and plates were incubated at 37° C. for 1 hour. After washing, attached cells were fixed and cell adhesion was measured as described in the methodology section.

(C) Cells were observed by phase contrast microscopy then photographed. Bar=50 µm.

Figure 13A:
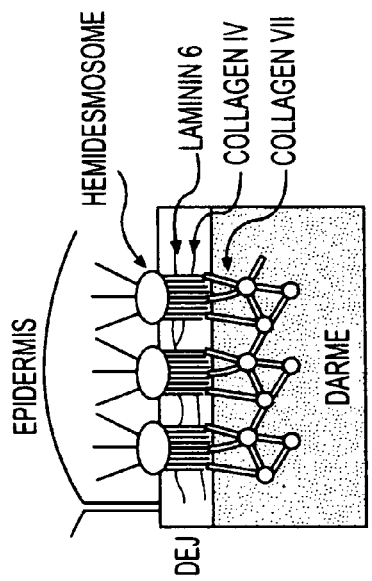

FIG. 13A illustrates the dermo-epidermal junction.

Figure 13C:
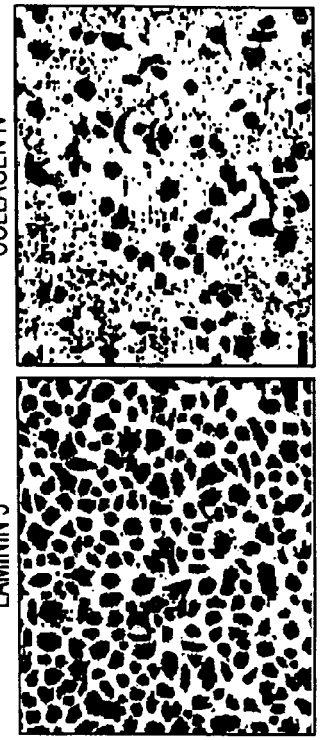
Figure 13B:
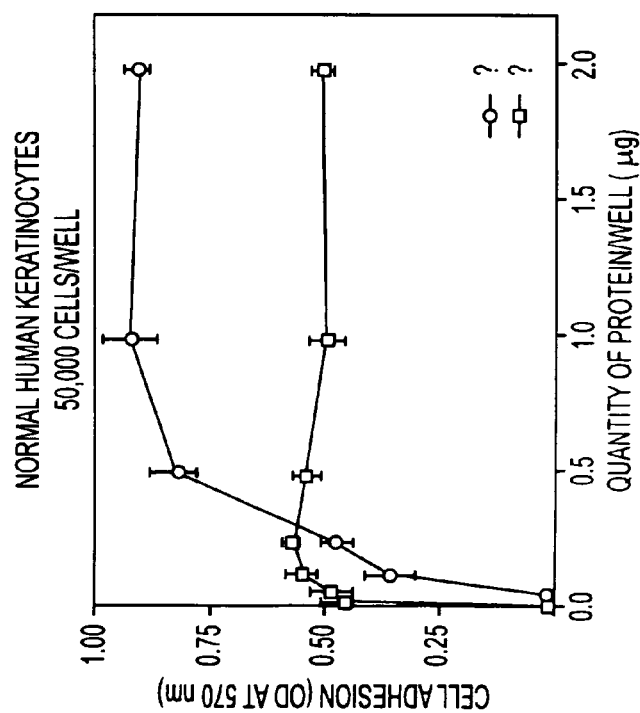

FIG. 13B is a graph of cell adhesion as a function of protein quantity.

FIG. 13C is the corresponding photographs of cells.

Figure 14:
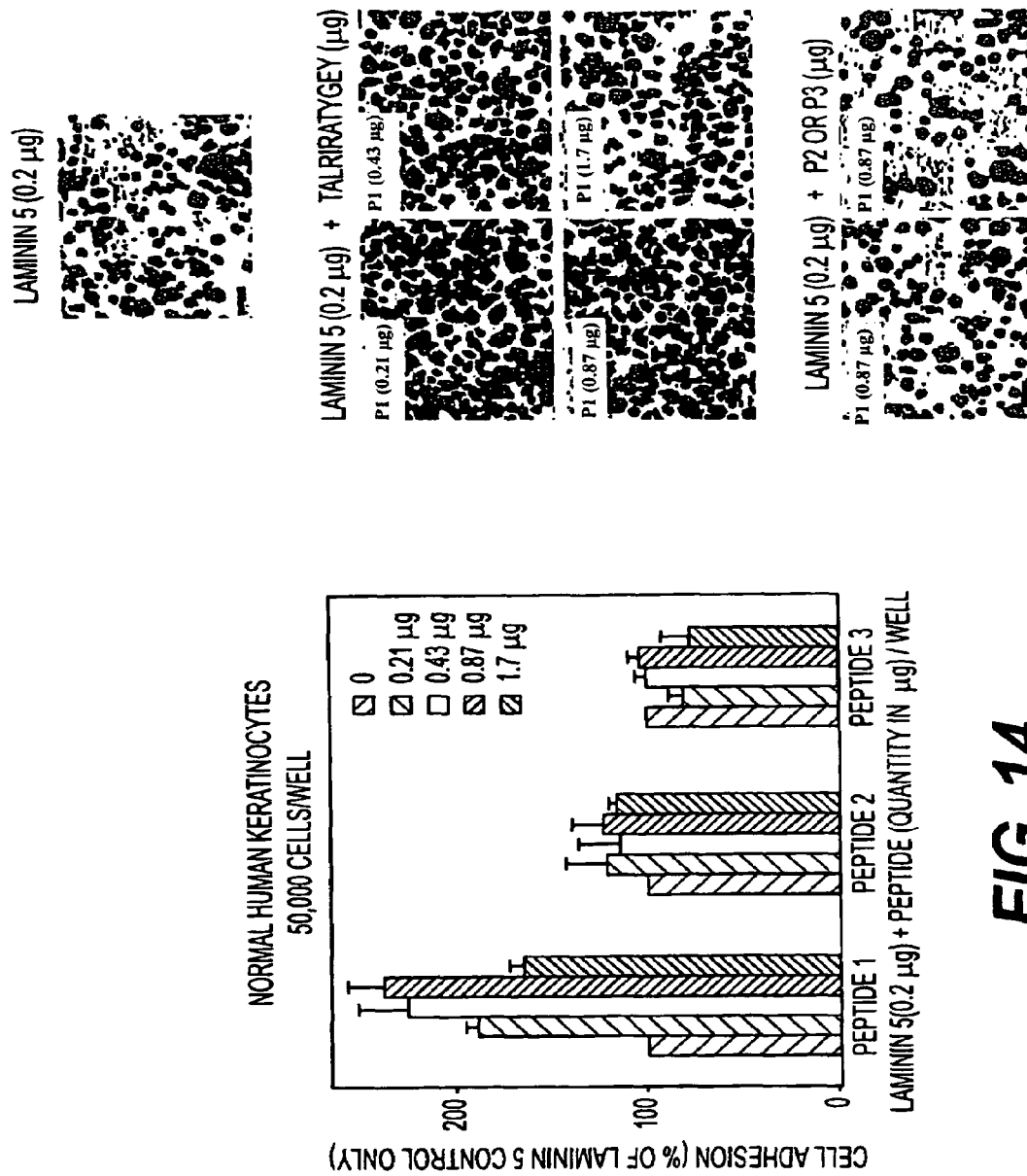

FIG. 14: Cell adhesion of NHKs to peptide TALRIRATYGEY (SEQ ID No. 1) co-immobilized with laminin 5

Peptides 1, 2 and 3 (variable quantities indicated) and laminin 5 (fixed quantity 0.2 mg) were co-immobilized in 96-well plates. $5 \times 10^4$ NHKs were deposited in each well and plates were incubated at 37° C. for 1 hour. After washing, attached cells were fixed and cell adhesion was measured as described in the methodology section. Cell adhesion in the presence of the peptide is given as a percentage of cell adhesion obtained with laminin 5 alone. Cells were observed by phase contrast microscopy then photographed. Bar=50 µm.

Figure 15:
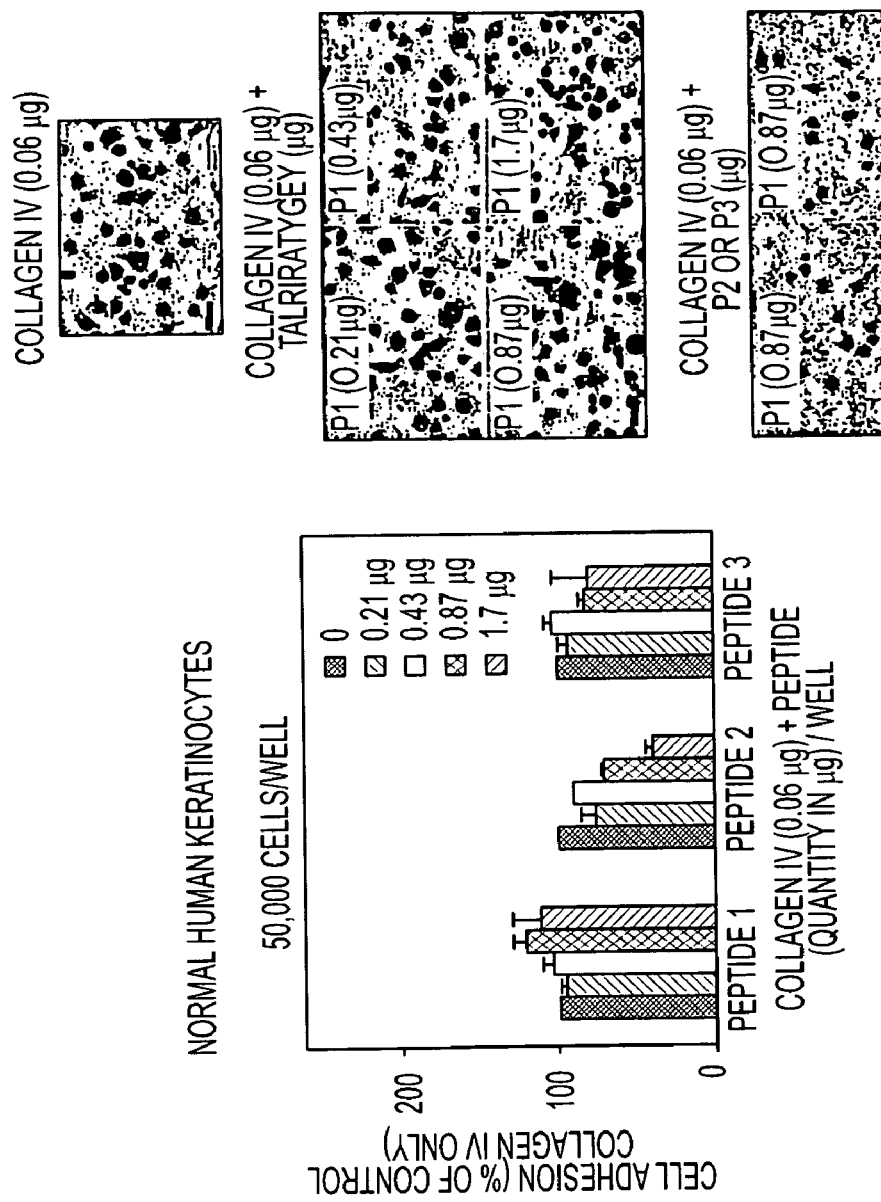

FIG. 15: Cell adhesion of NHKs to peptide TALRIRATYGEY (SEQ ID NO: 1) co-immobilized with collagen IV Peptides 1, 2 and 3 (variable quantities indicated) and collagen IV (fixed quantity 0.06 mg) were co-immobilized in 96-well plates. $5 \times 10^4$ NHKs were deposited in each well and plates were incubated at 37° C. for 1 hour. After washing, attached cells were fixed and cell adhesion was measured as described in the methodology section. Cell adhesion in the presence of the peptide is given as a percentage of cell adhesion obtained with collagen IV alone. Cells were observed by phase contrast microscopy then photographed. Bar=50 µm.

Figure 16:
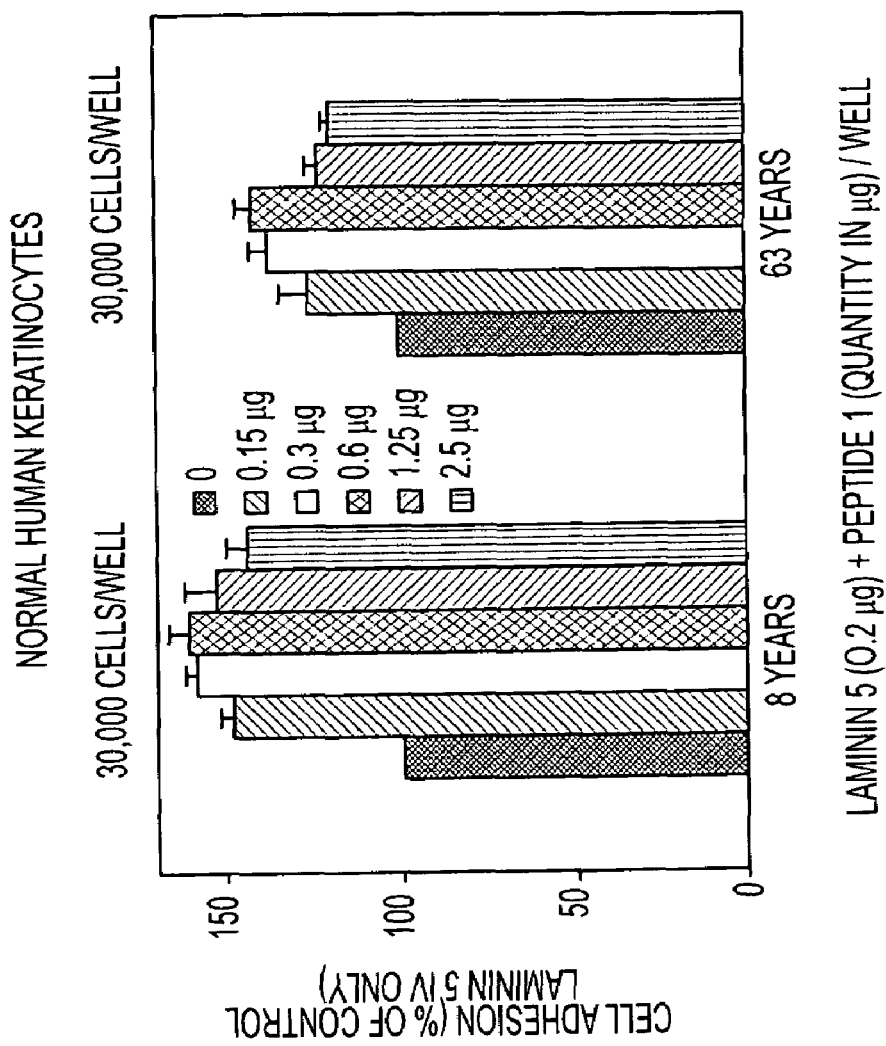

FIG. 16: Cell adhesion of NHK-young versus NHK-old to peptide TALRIRATYGEY (SEQ ID NO. 1) co-immobilized with laminin 5

The peptide (variable quantities indicated) and laminin 5 (fixed quantity 0.2 mg) were co-immobilized in 96-well plates. $3 \times 10^4$ NHK-8 years and $3 \times 10^4$ NHK-63 years were deposited in each well and plates were incubated at 37° C. for 1 hour. After washing, attached cells were fixed and cell adhesion was measured as described in the methodology section. Cell adhesion in the presence of the peptide is given as a percentage of cell adhesion obtained with laminin 5 alone.

FIG. 17

Summary table of doses of non-immobilized peptide TALRIRATYGEY (SEQ ID NO: 1) in 96-well plates.

FIG. 18

Summary table of doses of non-immobilized peptide TALRIRATYGEY (SEQ ID NO. 1) in 96-well plates.

Figure 19:
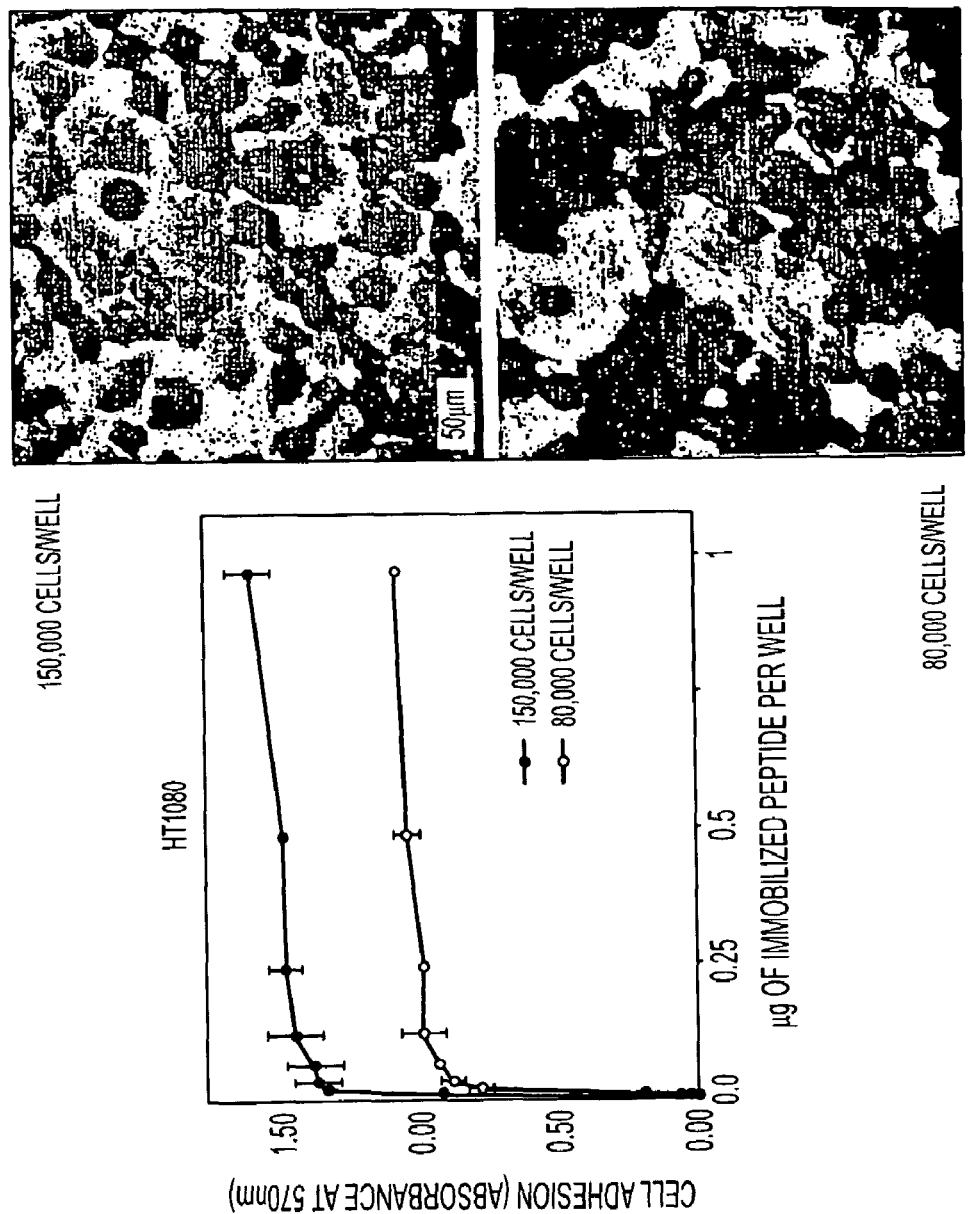

FIG. 19: Adhesion of HT1080 cells to peptide TALRIRATYGEY (SEQ ID NO. 1)

Figure 20:
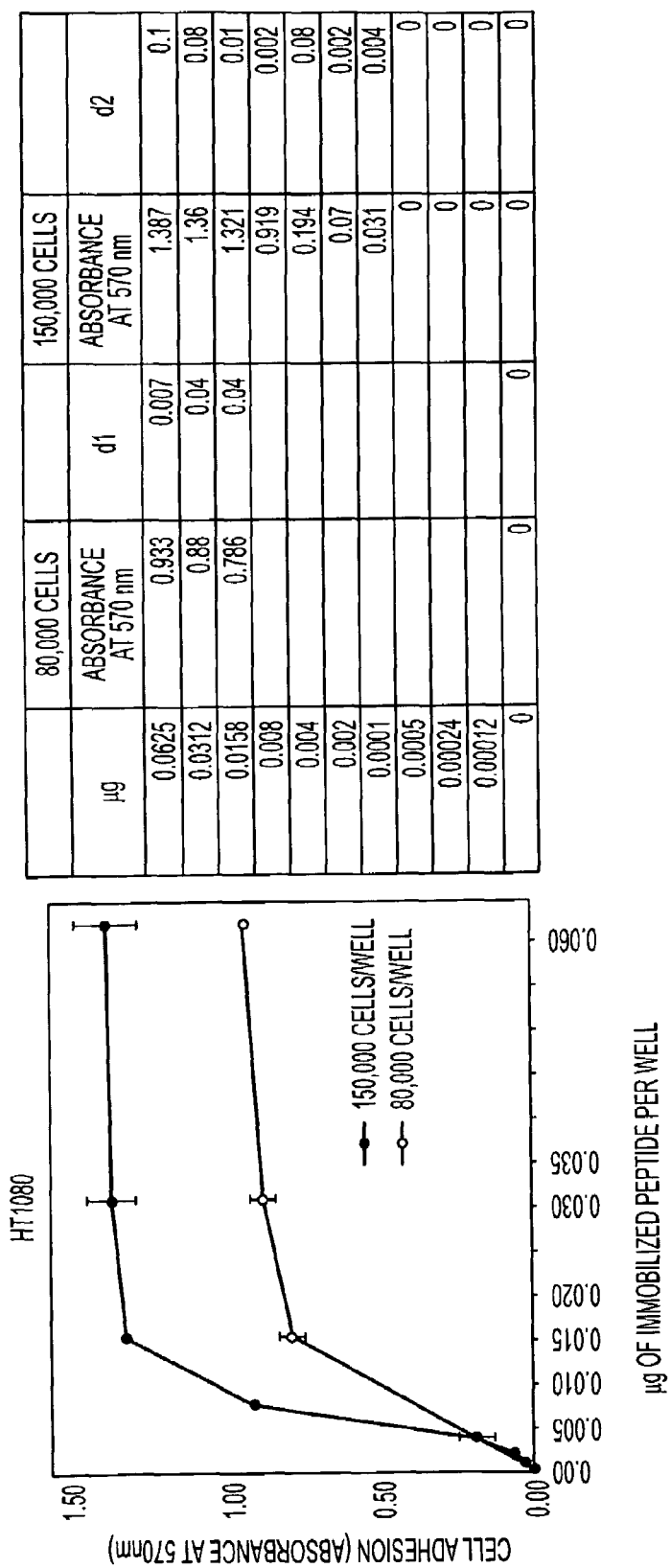

Dose-dependent cell adhesion of HT1080 cells to various peptide TALRIRATYGEY (SEQ ID NO. 1). The peptides were immobilized in 96-well plates in the quantities given on the abscissa. $8 \times 10^4$ cells and $15 \times 10^4$ cells were deposited in each well and plates were incubated at 37° C. for 1 hour. After washing, attached cells were fixed and cell adhesion was measured as described in the methodology section. Cells were observed by phase contrast microscopy then photographed. Bar =50 µm FIG. 20: Adhesion of HT1080 cells to peptide TALRIRATYGEY (SEQ ID NO. 1)

Dose-dependent cell adhesion of HT1080 cells to various peptide TALRIRATYGEY (SEQ ID NO. 1). The peptides were immobilized in 96-well plates in the quantities given on the abscissa. $8 \times 10^4$ cells and $15 \times 10^4$ cells were deposited in each well and plates were incubated at 37° C. for 1 hour. After washing, attached cells were fixed and cell adhesion was measured as described in the methodology section. Absorbance values at 570 nm are given in the table.

EXAMPLES

Example 1

Cell adhesion experiments were conducted on 3 peptides using cells commonly employed in cell adhesion studies, such as HT1080 (human fibrosarcoma), HBL100 (human mammary epithelium) and A431 (skin epitheloids) in order to demonstrate the specificity of adhesion of the peptide of the invention.

In addition to the peptide of the invention (peptide 1), two other peptides (peptide 2 and 3 corresponding to a gamma 2 chain sequence of laminin 5 but both differing from the sequence of the peptide of the invention) were synthesized and used as controls in the course of the cell adhesion experiments.

Figure 1:
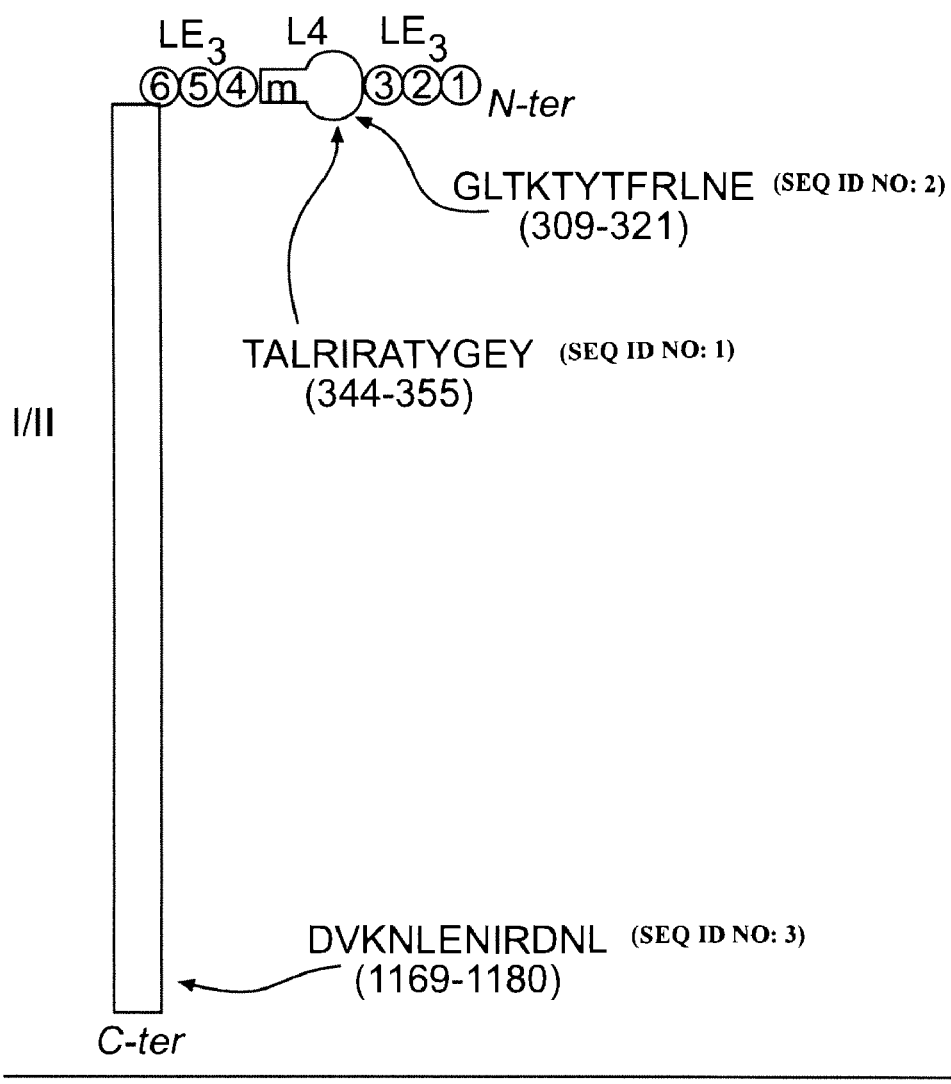
FIG. 1: Diagram of the gamma 2 chain of laminin 5 (155 kDa)

Peptides 1 and 2 are located at the terminal amino end of the "short arm" region of the gamma 2 chain (FIG. 1). The short arm of the laminins includes cysteine-poor sequences in a globular domain (domain L4m). This domain is surrounded by cysteine-rich repetitions arranged in the form of rods (L4 domains, 3 LE domains on each side). The latter consist of a 50-amino acid motif similar to epidermal growth factor (EGF-like domain). Peptide 3 was chosen from the terminal carboxy end. The terminal carboxy I and II domains are involved in the assembly of the three alpha, beta and gamma chains and form a super-coiled alpha helix which makes up the long arm of laminin. The sequence of interest is located in the L4m globular domain.

Dose-response effects were observed in the course of the cell adhesion experiments and the phenotype of attached cells was analysed by phase contrast microscopy (photographs).

I - Information concerning the peptide of
the invention: TALRIRATYGEY (SEQ ID No. 1)
Number of amino acids: 12
Molecular weight: 1413.6
Theoretical isoelectric point: 8.25

Amino acid composition

| | | |
|---|---|---|
| Ala (A) | 2 | 16.7% |
| Arg (R) | 2 | 16.7% |
| Asn (N) | 0 | 0.0% |
| Asp (D) | 0 | 0.0% |
| Cys (C) | 0 | 0.0% |
| Gln (Q) | 0 | 0.0% |
| Glu (E) | 1 | 8.3% |
| Gly (G) | 1 | 8.3% |
| His (H) | 0 | 0.0% |
| Ile (I) | 1 | 8.3% |
| Leu (L) | 1 | 8.3% |
| Lys (K) | 0 | 0.0% |
| Met (M) | 0 | 0.0% |
| Phe (F) | 0 | 0.0% |
| Pro (P) | 0 | 0.0% |
| Ser (S) | 0 | 0.0% |
| Thr (T) | 2 | 16.7% |
| Trp (W) | 0 | 0.0% |
| Tyr (Y) | 2 | 16.7% |
| Val (V) | 0 | 0.0% |
| Asx (B) | 0 | 0.0% |
| Glx (Z) | 0 | 0.0% |
| Zaa (X) | 0 | 0.0% |

Total number of negatively charged residues (Asp + Glu): 1
Total number of positively charged residues (Arg + Lys): 2

Atomic composition:

| | | |
|---|---|---|
| Carbon | C | 63 |
| Hydrogen | H | 100 |
| Nitrogen | N | 18 |
| Oxygen | O | 19 |
| Sulphur | S | 0 |

Formula: $C_{63}H_{100}N_{18}O_{19}$
Total number of atoms: 200

Extinction coefficient:

Conditions:

6.0 M guanidium hydrochloride
0.02 M phosphate buffer pH 6.5

Extinction coefficient units are $M^{-1} cm^{-1}$

| | 276 nm | 278 nm | 279 nm | 280 nm | 282 nm |
|---|---|---|---|---|---|
| Ext. coeff. | 2900 | 2800 | 2690 | 2560 | 2400 |
| Abs 0.1% (=1 g/l) | 2.051 | 1.981 | 1.903 | 1.811 | 1.698 |

Estimated half-life:

Terminal N of the sequence in question is T (Thr).
The estimated half-life is 7.2 hours (mammary reticulocytes, in vitro).
20 hours (yeasts, in vivo)
10 hours (*Escherichia coli*, in vivo)

Instability index:

The instability index is calculated to be 11.86
This classifies the protein as stable.
Aliphatic index: 81.67
Hydropathy mean: −0.417

II-Materials and Methods

1) Peptide Manufacturing Procedure

Peptide synthesis was carried out using a Milligen 9050 Synthesizer and Fmoc-Opfp/Hobt chemistry. The peptide was then analysed and purified on a Vydac C18 column (5 µm), diameter 4.6 or 10 mm and length 250 mm, then identified by electrospray mass spectrometry on a SCIEX API 165.

2) Peptides Sequence

Peptide 1: TALRIRATYGEY (SEQ ID No. 1)
Position 344-355 (FIG. 1)
Peptide 2: GLTKTYTFRLNE (SEQ ID No. 2)
Position 309-321 (FIG. 1)
Peptide 3: DVKNLENIRDNL (SEQ ID No. 3)
Position 1169-1180 (FIG. 1)

3) Quantitative Analysis of Cell Adhesion Properties of the Peptide of the Invention Using a Calorimetric Test Preparation Of Adhesion Substrates Peptides 1, 2 and 3 were used for the cell adhesion experiments. A range of 7 decreasing concentrations (100 micrograms/ml, 50 micrograms/ml, 25 micrograms/ml, 12.5 micrograms/ml, 6.25 micrograms/ml, 3.125 micrograms/ml and 1.562 micrograms/ml) was made up by successive dilution in PBS (Phosphate Buffer Saline, $KH_2PO_4$ 1.54 mM; $Na_2HPO_4$ 1.42 mM; NaCl-131 mM) using a starting solution at a concentration of 1 mg/ml. These solutions were immediately distributed onto a 96-well culture plate (Greinher, Dutscher, Brumath, France) at a rate of 100 µl per well. Plates were then placed at +4° C. for 16 to 18 hours. The solutions were then removed by turning the plates and each well was saturated with a 1% PBS-BSA solution (bovine serum albumin). Three additional wells without the substrate underwent the same treatment and were used as blanks.

Cell Adhesion Test

Epithelial cells were detached from the culture dishes using a trypsin/EDAT solution (0.05-0.02%) then suspended in DMEM medium without additives for the cell lines and in KBM-2 without additive for human keratinocytes. The number of seeded cells per well is given in the graphs (50,000 to 100,000 cells per well).

Evaluation of Cell Adhesion Test

After cell seeding, the multi-well plates were placed in an incubator at 37° C. under 5% CO2. After incubation for 30 to 60 minutes, cells were observed under a phase contrast microscope in order to verify that the test was conducted correctly. The adhesion medium was then removed and each well was washed in a sterile PBS solution to remove non-adhering cells. The remaining cells, attached to the substrate, were then fixed using a solution of 1% glutaraldehyde in PBS for 15 minutes. The glutaraldehyde solution as removed and the cells were stained with a crystal violet solution diluted to 1% in distilled water for 30 minutes.

After rinsing in water several times, cells were permeabilized by means of a 0.02% triton solution for 15 minutes in order to solubilize the crystal violet. Absorbances were read at 570 nm using an ELISA plate reader (MR500, Dynatech, Guernsey, Channel Islands). Each experimental point was carried out in triplicate. The blank value represented the mean absorbance of 3 control wells (BSA). This was subtracted from each of the optical density values for the experimental points. We then calculated the mean for the three absorbance values for each of the triplicate samples.

The results are presented in the form of a graph with the absorbance values on the ordinate and the various substrate concentrations on the abscissa. Attached cells were photographed by phase contrast microscopy.

4) Cells Used for the Study

A-Lines

The following cells from epithelial cell lines were used initially (commonly used in preliminary studies on cell adhesion):

line HT1080 cells (human fibrosarcoma), American Type Culture Collection CCL-121.

line HB100 cells (human mammary epithelium), American Type Culture Collection HTB-124.

line A431 cells (skin epitheliods), American Type Culture Collection CRL-1555.

These cells were kept in culture in DMEM medium supplemented with 10% foetal calf serum and 2 mM glutamine. They were cultured at 37° C. in a CO2 incubator (5% CO2, 95% air and 98% humidity).

B-Primary Keratinocytes

Freshly isolated normal human keratinocytes were used in a second experiment. As the basal keratinocytes of the epidermis are in direct contact with LN-5 in the skin, it was necessary to test their adhesion capacity to the peptide in question. Human keratinocytes were obtained from a foreskin biopsy (surgery waste, Pavillon T-Bis, Eduard Herriot Hospital). The culture medium used in the course of our work was the medium specified for culturing KBM-2 keratinocytes (containing: bovine pituitary extract 35 mg, hEGF 10 ng/ml, insulin 5 μg/ml, hydrocortisone 0.5 μg/ml, transferrin 0.1%, epinephrine 0.1%) manufactured by Clonetics and distributed by Cambrex (Belgium) obtaining 0.15 mM CaCl2, pH 7.2 to 7.4.

Keratinocytes were obtained by means of the technique described by Boyce and Ham (Cultivation, frozen storage and clonal growth of normal human epidermal keratinocytes in serum-free media, Tiss. Cult. Meth., 1985, 9:83-93). After careful washing in PBS buffer containing antibiotics, fatty tissue located under the dermis was removed from the skin fragments using sterile instruments. Skin was then cut into 3 mm$^2$ sections which were placed in a sterile solution of 0.25% trypsin in PBS for 16 hours at 4° C. Dermis/epidermis separation was performed using tweezers in a Petri dish containing culture medium in order to stop the enzyme action of tryspin. Epidermal fragments were then aspirated and blown out several times using a pipette in order to detach free basal cells. The cell suspension obtained in this manner was centrifuged at 5000 rpm for 5 minutes and the residue obtained was suspended in a known volume of KBM-2 in order to carry out a living cell count with the aid of an exclusion dye, trypan blue. $3 \times 10^4$ living cells per cm$^2$ were seeded in 25 cm$^2$ tissue culture dishes (Corning, Polylabo, France). Keratinocytes were incubated at 37° C. in a CO2 incubator (5% CO2, 95% air and 98% humidity). The medium was changed every two days. Subcultures were made when cells reached subconfluence. The cell network was then rinsed with PBS then covered with a Trypsin-EDTA solution (0.05-0.02%). After a short incubation period at 37° C., cells became detached from the plastic support. Cells were then seeded in 75 cm$^2$ culture dishes. Cell freezing (3 to 5 million per vial) was carried out in the culture medium used with 10% dimethyl sulfoxide (DMSO) and 20% calf serum in a volume of 1 ml.

III-Results

The cell adhesion experiments presented in FIGS. 1 to 5 were carried out with the following quantities of immobilized peptides: 0, 0.15, 0.31, 0.62, 1.25, 2.5, 5 and 10 micrograms. Two different batches of peptide 1 were tested in parallel. Peptides 2 and 3 are the control peptides. Peptide 2 was voluntarily selected in a region close to peptide 1 in the L4 domain of the gamma 2 chain and peptide 3 in a distant region. Peptide 1 (peptide of the invention) led to cell adhesion of the various epithelial cell lines tested, HBL100 (FIG. 2), HT1080 (FIG. 3) and A431 (FIG. 4), in an increasing manner as a function of the quantity of immobilized peptide (0 to 10 micrograms). This effect also occurred with epidermal cells, normal human keratinocytes (FIG. 5). The cells were solidly anchored to the peptide because they resisted several washes prior to fixation. The other two peptides (peptides 2 and 3), chosen randomly from the same protein, did not lead to any adhesion, whatever the quantity immobilized. Adhesion of normal human keratinocytes occurred at an immobilized peptide 1 quantity of 0.15 micrograms and maximum adhesion was achieved at an immobilized peptide quantity of 0.62 micrograms (FIG. 5). Adhesion of HBL100 occurred at an immobilized peptide 1 quantity of 0.31 micrograms and maximum adhesion was achieved at an immobilized peptide quantity of 1.25 micrograms (FIG. 2). Adhesion of HT1080 occurred at an immobilized peptide 1 quantity of 0.15 micrograms and maximum adhesion was achieved at an immobilized peptide quantity of 0.15 micrograms (FIG. 3). Adhesion of A431 occurred at an immobilized peptide 1 quantity of 0.62 micrograms and maximum adhesion was achieved at an immobilized peptide quantity of 1.2 micrograms.

The photographs obtained by phase contrast microscopy confirmed the quantitative results and absence of cells attached to control peptides 2 and 3. Cells attached to peptide TALRIRATYGEY (peptide of the invention) generally show a rounded morphology with frequent cell groupings (FIGS. 2, 3, 4 and 5). These groupings might indicate cell-cell interactions. Cell extensions were also noted, most visible in the case of HBL100 (FIG. 2), HT1080 (FIG. 3) and normal human keratinocytes (FIG. 5) and harder to see in the case of A431 as the cells are smaller. These cell extensions might indicate a re-ordering of the cell cytoskeleton in response to adhesion to the peptide. The results were confirmed with normal human keratinocytes (epidermal cells, FIG. 5).

Example 2

I. Materials and Methods
1) Cell Cultures
a) Cell Lines and Normal Human Keratinocytes (see Example 1)
b) Obtaining and Culturing Young and Old Keratinocytes In order to obtain keratinocytes originating from biopsies taken from young and old individuals and taken from the same anatomical site, the inventors conducted a study of facial skin biopsies. The area of the face situated behind the ears was chosen in order to study only intrinsic aging and to overcome the effects of photo-induced aging. Surgery waste from cosmetic surgery (face lifts) in older individuals and surgery waste from detached ears in young children was collected. It is essential to use biopsies collected on the same day as surgery was performed in order to quickly place the epidermal keratinocytes in culture. Cells from biopsies on elderly individuals (60, 63 and 71 years) and young individuals (8, 10 and 11 years) were used for this study. The keratinocytes were obtained by means of the technique described by Boyce and Ham, 1985. After careful washing in PBS buffer containing antibiotics, fatty tissue located under the dermis was removed from the skin fragments using sterile instruments. Skin was then cut into 3 mm$^2$ sections which were placed in a sterile solution of 0.25% trypsin in PBS for 16 hours at 4° C. Dermis/epidermis separation was performed using tweezers in a Petri dish containing culture medium in order to stop the enzyme action of trypsin. Epidermal fragments were then aspirated and blown out several times using a pipette in order to detach free basal cells. The cell suspension obtained in this manner was centrifuged at 5000 rpm for 5 minutes and the residue obtained was suspended in a known volume of KBM-2 in order to carry out a living cell count with the aid of an exclusion dye, trypan blue. $3\times10^4$ living cells per cm$_2$ were seeded in 25 cm$^2$ tissue culture dishes (Coming, Polylabo, France). Keratinocytes were incubated at 37° C. in a CO2 incubator (5% CO2, 95% air and 98% humidity). The medium was changed every two days. Subcultures were made when cells reached subconfluence. The cell network was then rinsed with PBS then covered with a Trypsin-EDTA solution (0.05-0.02%). After a short incubation period at 37° C., cells became detached from the plastic support. Cells were then seeded in 75 cm$^2$ culture dishes. Cell freezing (3 to 5 million per vial) was carried out in the culture medium used with 10% dimethyl sulfoxide (DMSO) and 20% calf serum in a volume of 1 ml. After defrosting, cells were seeded at a rate of 10,000 cells/cm$^2$.

2) Cell Adhesion Tests

Dose-response cell adhesion of young and old cells to peptide TALRIRATYGEY (SEQ ID NO.1)

A range of 7 decreasing concentrations of TALRIRATYGEY (SEQ ID NO 1) was made up by successive dilution in PBS (Phosphate Buffer Saline, KH2PO4 1.54 mM; Na2HPO4 1.42 mM; NaCl 131 mM) using a starting solution at a concentration of 1mg/ml. These solutions were immediately distributed onto a 96-well culture plate (Greinher, Dutscher, Brumath, France) at a rate of 100 μl per well. Plates were then placed at +4° C. for 16 to 18 hours. The solutions were then removed by turning the plates and each well was saturated with a 1% PBS-BSA solution (bovine serum albumin). Three additional well without the substrate underwent the same treatment and were used as blanks.

Keratinocytes from young and elderly individuals were detached from the culture dishes by means of a trypsin/EDTA solution (0.05-0.02%) then suspended in KBM-2. The number of cells seeded per well is given on the graph. The same number of young/old cells were used for comparative experiments.

After cell seeding, the multi-well plates were placed in an incubator at 37° C. under 5% CO2. After incubation for 30 to 60 minutes, cells were observed under a phase contrast microscope in order to verify that the test was conducted correctly. The adhesion medium was then removed and each well was washed in a sterile PBS solution to remove non-adhering cells. The remaining cells, attached to the substrate, were then fixed using a solution of 1% glutaraldehyde in PBS for 15 minutes. The glutaraldehyde solution as removed and the cells were stained with a crystal violet solution diluted to 1% in distilled water for 30 minutes. After rinsing in water abundantly, cells were permeabilized by means of a 0.02% triton solution for 15 minutes in order to solubilize the crystal violet. Absorbances were read at 570 nm using an ELISA plate reader (MR500, Dynatech, Guernsey, Channel Islands). Each experimental point was carried out in triplicate. The blank value represented the mean absorbance of 3 control wells (BSA). This was subtracted from each of the optical density values for the experimental points. We then calculated the mean for the three absorbance values for each of the triplicate samples.

The results are presented in the form of a graph with the absorbance values on the ordinate and the various substrate concentrations on the abscissa. Attached cells were photographed by phase contrast microscopy.

II. Results and Discussion

Cell Adhesion of NHK-Young and NHK-Old

Given that skin aging is characterised by a deficiency in cell-extracellular matrix interactions, it was necessary to verify the capacity of keratinocytes originating from elderly individuals to attach to the peptide of interest. Two comparative experiments on cell adhesion of "NHK-young-versus NHK-old" to peptide TALRIRATYGEY (SEQ ID NO.1) were conducted (FIG. 6). Experiments were performed using the following peptide quantities: 0, 0.08, 0.15, 0.30, 0.6, 1.25, 2.50 and 5 micrograms per well. For each of these two experiments, NHK-young and NHK-old numbers were identical in order to allow comparison of the results obtained. One experiment was performed using keratinocytes originating from a skin biopsy from a 10year-old child and one from a 71-year-old adult (FIG. 6A) while the second experiment used keratinocytes originating from a skin biopsy from an 11-year-old child and one from a 60-year-old adult (FIG. 6B). Peptide TALRIRATYGEY (SEQ ID NO.1) triggered dose-dependent cell adhesion of NHK-young and NHK-old. In both experiments, it was found that a greater number of NHK-young (approximately ×2) cells are attached compared to NHK-old. This result suggests that the cell receptor recognizing peptide TALRIRATYGEY (SEQ ID NO.1) might decrease with age. The interesting point is that it is always expressed significantly and that it is functional since the dose-response effect of the peptide on NHK-old is identical to the dose effect found for NHK-young. The photos obtained by phase contrast microscopy confirm the quantitative results. NHK-young attached to peptide TALRIRATYGEY (SEQ ID NO.1) generally shows a rounded morphology with frequent cell groupings (as described in example 1) while there are fewer cells in the case of NHK-old. Adhesion of NHK-young is triggered for a deposited peptide quantity of 0.08 μg and while that of NHK-old is triggered for a deposited peptide quantity ranging from 0.08 to 0.15 µg. The adhesion plateau is reached in the range 0.3 to 0.6 micrograms of deposited peptide per well.

Example 3

I. Materials and Methods

1) Cell Cultures a) Cell Lines and Normal Human Keratinocytes (See Example 1)

b) Obtaining and Culturing Young and Old Keratinocytes (see Example 2)

2) Cell Proliferation Test

The effect of the peptide on cell proliferation was analysed with the aid of a calorimetric test (Cell Proliferation Kit XTT, Roche Diagnostics, Meylan, France) on the cells use for the cell adhesion test, i.e. HT1080, A431, HBL100 cells and normal human keratinocytes from young and elderly individuals.

The chemical reaction used in the test is based on the production of NADPH by living cells, leading to the reduction of yellow tetrazolium XTT salts to orange formazan salts. Absorbance was measured at 490 nm using an ELISA plate reader. Cells were seeded in 96-well plates at a rate of 10,000 cells per well (6 wells/condition) in KBM-2 culture medium. After 24 hours in culture at 37° C. with 5% CO2, the culture medium was removed and replaced with serum-free medium containing the peptide quantities given in the graphs and the test reagent. The plates were then placed in the incubator at 37° C. and absorbance readings were taken at 1 h, 2 h, 3 h, 4 h and 5 h. Peptide-free controls were carried out on the same plate. Results are given in two forms:

either as graphs showing the change in absorbance as a function of time or in the form of percentage viability of cells in contact with the peptide compared to the peptide-free controls. In this case, cell viability was calculated according to the following formula:

% viability=(Abs. Cells with peptide/Abs. Control cells)×100.

3) Study of the Effect of the Peptide in Soluble Form on Keratinocyte Behaviour

Keratinocytes were seeded in 12-well plates (Costar) at a rate of 5,000 cells per well in KBM-2 medium. After 24 hours in culture at 37° C. with 5% CO2, the culture medium was removed and replaced with KBM-2 medium containing the peptide quantities given in the figures (a peptide-free control was also carried out). After 24 hours in culture, the same quantity of peptide was added to the culture medium and the experiment was stopped after a further 24 hours in culture. Microscope analyse was carried out without preliminary fixation using an Axiovert 40 Zeiss microscope coupled to a Coolsnap camera (Roper Scientific, Evry, France).

II. Results and Discussion

1-Effect of the Peptide on Cell Proliferation

In order to analyse the effect of peptide TALRIRATYGEY (SEQ ID NO.1) on cell proliferation, the inventors initially analysed the effect of different concentrations (0.5% and 1%) on HT1080, HBL100 and A431 cells (FIGS. 7, 8 and 9). The cells were seeded at a rate of 10,000 cells per well. After 24 hours in culture, the culture medium was removed and replaced with serum-free medium containing the peptide quantities given in the graphs and the test reagent. The plates were then placed in the incubator at 37° C. and absorbance readings were taken at 1 h, 2 h, 3 h, 4 h and 5 h. Peptide-free controls were carried out on the same plate. A moderate but constant increase in cell proliferation in cells from lines HT1080 (FIG. 7A), HBL100 (FIG. 7B) and A431 (FIG. 8) was noted as a function of time and attained a mean increase of 8% at the $5^{th}$ hour compared to the control. Longer times were tested but the effect was no more pronounced. No difference was noted between the two peptide concentrations tested, whatever the cell type tested. The test was then conducted with NHK-young and NHK-old (FIG. 9). The quantities of peptide added were reduced (0.05% and 0.1%) with the aim of carrying out the test in a concentration range closer to the conditions of use of the peptide in the adhesion test. Once again, a moderate and regular increase in proliferation was found, reaching a mean increase not exceeding 7% at the $5^{th}$ hour compared to the control. No significant difference was found in terms of the concentrations used or cell age. A last series of tests was performed on NHKs for a broader range of peptide concentrations and for a longer time (24 h) (FIG. 10). The results are given in the form of percentage viability of cells contacted with the peptide for 24 h compared to the peptide-free controls. In this experiment, an increase in cell proliferation was noted ranging from 6 to 13% as a function of peptide concentration (0.004% to 0.37%).

2-Study of the Effect of the Peptide in Soluble Form on the Behaviour of Keratinocytes in Culture Peptide TALRIRATYGEY (SEQ ID NO.1) triggers cell adhesion when it is fixed to 96-well plates (Examples 1 and 2). We wanted to ascertain whether it was capable of affecting the behaviour of keratinocytes when added to the culture medium. To do this, NHKs were seeded in 12-well plates at a rate of 5,000 cells per well. After 24 hours, the culture medium was removed and replaced with new medium containing 5%, 2.5%, 1.25%, 0.6% and 0.3% peptide. A peptide-free control was also carried out. The plates were then placed in the incubator at 37° C. for 48 hours and the process was repeated once every 24 hours of additional culturing. In the control well (without addition of the peptide), NHKs were in general still isolated and starting to assemble into colonies (FIG. 11A). It was found that NHKs cultured with the peptide were already assembled into larger-sized, easily identifiable colonies (FIG. 11B-F). Observation of these colonies at a higher magnification (FIG. 12) showed that cells cultured with the peptide formed a linked, cohesive network. There was no morphological difference between cells cultured with the peptide (FIG. 12B,C) and control cells (FIG. 12A). Nevertheless, addition of the peptide to the NI-IK medium led to faster formation of cohesive colonies. This effect may be the result of the slight increase in cell proliferation triggered by the peptide.

Example 4

I. Materials and Methods

1) Cell Cultures a) Cell Lines and Normal Human Keratinocytes (See Example 1)

b) Obtaining and Culturing Young and Old Keratinocytes (See Example 2)

2) Cell adhesion test

Analysis of the Effect of the Peptide of Interest on the Adhesion of Keratinocytes to Laminin 5 (Ln 5) and Collagen Iv (COL4)

A decreasing range of LN5 (prepared in the laboratory) and COL4 (BD Biosciences, Le Pont de Claix, France) quantities was made up by successive dilution in PBS. These solutions were immediately distributed into a 96-well culture plate (Costar) at a rate of 100 µl per well. The experiment was conducted in exactly the same way as the experiment described in example 2. The results are given in the form of a graph with the absorbance values representing adhesion on the ordinate and the various substrate concentrations on the abscissa. Attached cells were photographed by phase contrast microscopy.

II. Results and Discussion

Analysis of the Effect of the Peptide of Interest on the Adhesion of Keratinocytes to Laminin 5 and Collagen IV The base molecular network of the dermo-epidermal junction (DEJ) is made up of an assembly of collagen IV (COL4) molecules. This molecular network leads to the formation of a loosely meshed net with a polygonal structure acting as the framework to secure other basal proteins (FIG. 13A). A second molecular network is made up of laminin molecules. Laminin 5 (LN5) is quantitatively the most abundant glycoprotein in the dermo-epidermal junction and constitutes the anchorage filaments. LN5 plays a crucial and irreplaceable role in epidermal adhesion through its interaction with the integrins. In order to analyse the effect of peptide TALRIRATYGEY (SEQ ID NO.1) in the context of the DEJ, the inventors carried out co-immobilization experiments of the peptide with LN5 and COL4 and analysed the adhesion capacity of keratinocytes. In order to define the experimental conditions, adhesion experiments to the substrates (LN5 and COL4) were initially carried out using 0, 0.03, 0.06, 0.125, 0.25, 0.5, 1 and 2 micrograms per well. As described widely in the literature and illustrated in FIG. 13B, the two proteins tested led to adhesion of NHKs but LN5 is a much better substrate. The photographs obtained with phase contrast microscopy confirm the quantitative results and show that LN5 leads to the formation of a cohesive epithelial network while COL4 leads to less adhesion (FIG. 13C). For the rest of the experiment, substrate quantities (LN5 and COL4) triggering average adhesion were chosen from the graphs given in FIG. 13B: 0.2 microgram of LN5 and 0.03 microgram of COL4.

In order to analyse the effect of the peptide on cell adhesion to DEJ proteins, peptide TALRIRATYGEY (SEQ ID NO.1) (peptide 1) was co-immobilized with LN5 (FIG. 14) and COL4 (FIG. 15). The fixed quantity of matrix protein (LN5 and COL4) and the variable quantity of peptide are given on the graph (FIGS. 14 and 15). Peptides 2 and 3 (described in example 1) were used as controls for the experiment. The adhesion tests were carried out with NHK under the same conditions as the experiment given in FIG. 13 (50,000 cells per well). A peptide-free control representing 100% adhesion (LN5 only and COL4 only) was used to allow analysis of the effect of adhesion relating to the presence of the peptide. The results are given as a percentage of this control.

As shown in FIG. 14, peptide TALRIRATYGEY (SEQ ID NO.1) leads to a gradual and significant increase in the adhesion of NHKs to LN5. On average, adhesion to LN5 is doubled for a peptide quantity of 0.21 to 0.87 µg/well. This effect is specific because it is not found with control peptides 2 and 3. The photographs obtained with phase contrast microscopy confirm the quantitative results and show that LN5 used alone at 0.2 mg leads to average adhesion. The addition of peptide P1 leads to the formation of a confluent cell network whereas peptides P2 and P3 do not modify adhesion obtained with LN5 only. The same experiment carried out with COL4 (FIG. 15) shows no significant effect of peptide TALRIRATYGEY (SEQ ID NO.1) on the adhesion of keratinocytes to COL4.

This set of results indicates that peptide TALRIRATYGEY (SEQ ID NO: 1) potentialises the adhesion of NHKs to LN5 when these two proteins are co-present.

The effect of peptide TALRIRATYGEY (SEQ ID NO. 1) on adhesion to LN5 was verified with NHK-old (FIG. 16). NHK-young (8 years) was tested in parallel and 30,000 cells/well were used in both cases (NHK-old is always limiting as it is obtained in lower amounts). In general, the results obtained in the course of this experiment are less marked than those in the experiment presented in FIG. 14 since (1) the number of cells is lower (30,000 instead of 50,000) and (2) the peptide range tested is also smaller. However, peptide TALRIRATYGEY (SEQ ID NO.1) was found to have a potentializing effect on the adhesion of NHK-old to LN5. This effect, less marked than the effect found with NHK-young, is probably linked to the decreased adhesion with age of NHK-old to peptide TALRIRATYGEY (SEQ ID NO.1) (FIG. 6).

Example 5

Determination of the Minimum Quantity of Peptide Leading to Cell Adhesion

I. Materials and Methods

1) Production of the Peptide

The peptide was produced as described in example 1. Peptide synthesis was carried out using a Milligen 9050 Synthesizer and Fmoc-Opfp/Hobt chemistry. The peptide was then detached from the resin and deprotected using a TFA solution (trifluoracetic acid) containing scavenger (phenol, water, ethanedithiol and thioanisole). The peptide was then analysed and purified on a Vydac C18 column, 5 mm, diameter 4.6 or 10 mm and length 250 mm, then identified by electrospray mass spectrometry on a SCIEX API 165.

2) Determination of the Quantity of Peptide Immobilized on the Plates Using the Amino Acid Analysis Method The peptide was diluted in sterile PBS. Samples containing the peptide to be assayed were lyophilized by evaporation. They were deposited in a reactor and placed under vacuum in order to eliminate oxygen likely to oxidize certain amino acids. Hydrolysis of the peptide bonds was carried out in a hydrochloric acid mixture (HCL 6N, $\frac{2}{3}$), trifluoroacetic acid (TFA, $\frac{1}{3}$) at 150° C. for 45 minutes. Gas hydrolysis prevented contamination by ions present in the acids. The samples were then dried and dissolved in a suitable buffer for ion-exchange chromatography (sodium citrate). Ion-exchange chromatography makes it possible to separate amino acids according to their ionic strength and, on leaving the column, they react with a reagent (ninhydrin) to form a dyed complex with primary amines (violet, readable at 570 nm). Ninhydrin also reacts with secondary amines (proline, hydroxyproline) to form a yellow compound that can be read at 440 nm. Two separate chromatograms allow the samples to be analysed.

A semi-automatic Beckman 6300 analyser optimised for this analysis was used along with Beckman Gold software in order to quantify the chromatograms. The results were transferred to an MS-Excel table with a macro to enable calculation of relative compositions.

3) Cell cultures a) Cell Lines and Normal Human Keratinocytes (See Example 1)

b) Obtaining and Culturing Young and Old Keratinocytes (see Example 2)

4) Cell Adhesion Test (See Example 2)

II. Results and Discussion

Determination of the quantity of peptide immobilized on 96-well plates

The cell adhesion experiments conducted with the peptide require a preliminary step to immobilize the peptide on 96-well plates. This step is carried out by contacting the solution containing the peptide with the plastic surface for 18 hours at +4° C. The solutions were then removed by aspiration and the peptide is immobilized on the surface, ready to interact with cells added during the cell adhesion test itself. Depending on the physicochemical properties of the peptides or proteins used, a varying percentage is actually immobilized on the support. It was therefore necessary to ascertain the precise percentage peptide TALRIRATYGEY (SEQ ID NO.1) immobilization in order to know the actual amount of peptide that triggers adhesion.

FIG. 17 gives the data obtained in the experiments aimed at identifying the assay conditions for the peptide deposited in 96-well plates and not immobilized. Five experiments were carried out with decreasing quantities of peptide, from 5 μg to 0.7 μg. For each condition, a given quantity of peptide was deposited in 3 different wells (100 μg/well) on a 96-well plate. After contact for 18 hours at +4° C., the supernatants were collected and deposited in tubes and assayed by the method for determining amino acid composition. Two identical samples of the solution used for the deposits were re-assayed under the same conditions. The first experiments carried out using 5.19 μg show that the quantity of immobilized peptide is very low. The results obtained for this condition could not be used since the values in the supernatants were sometimes higher than those of the starting solution. This further signifies that the difference between starting quantity and supernatant quantity was too low to be detected and was certainly within the deviation range from the assay mean for the starting solution. The experiment was therefore repeated with lower quantities of peptide deposited in the wells: 3.55 μg, 2.56 μg, 1.23 μg and 0.73 μg. These quantities of peptide were sufficient to carry out the experiment since we obtained equivalent results for these four conditions. The quantity of peptide remaining in the supernatant after immobilization is approximately 90% of the quantity of peptide added.

A second step involved using two different peptide quantities (Q1 and Q2) to carry out the assay on a larger number of samples (FIG. 18). Two Q1 samples (2×100 μl) and two Q2 samples (2×100 μl) were deposited directly in special tubes intended for assaying the two starting solution using the amino acid determination technique. Five different wells on the 96-well plate received quantity Q1 (volume 100 μl) and five other well received quantity Q2 (volume 100 μl). After 18 hours at +4° C., the five supernatants from the Q1 wells and the five supernatants from the Q2 wells were collected in special glass tubes for amino acid assays. All samples, starting solutions and supernatants were assayed at the same time. The assay made it possible to assay an average quantity of 2.44 μg in Q1. Assays of the five supernatants showed a mean quantity of 2.212 μg remaining in solution in the wells, in other words 90.7% of the peptide remained in solution after immobilization. This signifies that only 9.3% of the peptide was immobilized. A similar percentage was found for quantity Q2 whose mean starting quantity was 1.09 μg. After the immobilization step, the assay found a mean quantity of 1.002 μg in the supernatants, signifying that 92% of the peptide quantity was not immobilized.

These results make it possible to conclude that only 8 to 9% of the initial quantity of peptide added to the wells was immobilized.

This quantity is well below the initial quantity added to the well, making it possible to determine with precision the minimum quantity of truly active peptide.

A second approach was taken in order to determine the minimum quantity of active peptide and the number of adhering cells was increased in order to obtain a confluent cell network. HT1080 cells were chosen for this experiment as they have the same adhesion profile as keratinocytes. The adhesion test conditions are the same as those described previously. The graphs for adhesion to the peptide under the two seeding conditions are given in FIG. 19. Two cell cultures were tested: 80,000 cells per well (100 μg/well) and 150,000 cells per well (100 μg/well). As shown in FIG. 19, the two graphs are parallel and reach an adhesion plateau for the same amount of immobilized peptide. The difference found between the two graphs relates to the difference in absorbance intensity which is greater in the case of double the amount of cells. The images illustrate a homogeneous and confluent cell network on the right, obtained when 150,000 cells were seeded. The cells are joined and associated with each other. It should be noted that the peptide leads to cellular distribution and cell-cell junctions, providing good cell communication.

The ascending section of the graph was analysed to determine the minimum quantity of peptide leading to significant adhesion (FIG. 19). The 150,000 cells per well culture shows that the minimum quantity of peptide triggering significant adhesion is situated in the range of 0.008 μg to 0.015 μg.

Example 6

Examples of Compositions Containing Peptide

| Ingredients | % |
| --- | --- |
| Aqua (Water) | qs for 100 |
| Hexyl Laurate | 37.000 |
| Glycerin | 5.000 |
| Methyl Glucose Isostearate | 3.500 |
| Dimethicome | 3.000 |
| Disteardimonium Hectorite | 3.000 |
| Euphorbia Ceriefra (Candelilla) Wax | 1.500 |
| PEG-45/Dodecyl Glycol Copolymer | 1.000 |
| Phenoxyethanol | 0.580 |
| Methylparaben, Ethylparaben, Butylparaben, Propylparaben, Isobutylparaben | 0.420 |
| Chlorphenesin | 0.280 |
| Magnesium Sulfate | 0.100 |
| Disodium EDTA | 0.100 |
| Peptide TALRIRATYGEY (SEQ ID No. 1) | 0.0001 |

| Ingredients | % |
| --- | --- |
| Aqua (Water) | qs for 100 |
| Cyclomethicone | 4.000 |
| Glycerin | 3.000 |
| Hydrogenated Polyisobutene | 3.000 |
| PPG-15 Stearyl Ether | 2.000 |
| Ethyl Pamitate | 2.000 |
| Steareth-2 | 2.000 |
| Steareth-21 | 1.750 |
| Cetyl Alcohol | 1.500 |
| Phenoxyethanol, Methylparaben, Ethylparaben, Butylparaben, Propylparaben, Isobutylparaben | 0.600 |
| Polyacrylamide, C13-14 Isoparaffin, Laureth-7 | 0.400 |
| Xanthan Gum | 0.300 |
| Chlorphenesin | 0.200 |
| Peptide TALRIRATYGEY (SEQ ID No. 1) | 0.001 |

| Ingredients | % |
|---|---|
| Aqua (Water) | qs for 100 |
| Glycerin | 5.000 |
| Propylene Glycol, Aqua (Water), Benzoic Acid, Phenoxyethanol, Methylparaben, Ethylparaben, Butylparaben, Propylparaben, Isobutylparaben, PEG-40, Hydrogenated Castor Oil | 1.250 |
| Bis-EG-18 Methyl Ether Dimethyl Silane | 0.500 |
| Tetrasodium EDTA | 0.200 |
| Peptide TALRIRATYGEY (SEQ ID No. 1) | 0.0003 |

| Ingredients | % |
|---|---|
| Aqua (Water) | qs for 100 |
| Cyclomethicone | 4.000 |
| Glycerin | 3.000 |
| Phenoxyethanol, Methylparaben, Ethylparaben, Butylparaben, Propylparaben, Isobutylparaben | 0.600 |
| Polyacrylamide, C13-14 Isoparaffin, Laureth-7 | 0.500 |
| Carbomer | 0.500 |
| Chlorphenesin | 0.200 |
| Peptide TALRIRATYGEY (SEQ ID No. 1) | 0.003 |

The invention claimed is:

1. A peptide consisting of the following sequence: TALRIRATYGEY (SEQ ID NO:1).

2. The peptide of claim 1, wherein it is obtained by chemical synthesis.

3. A pharmaceutical composition comprising the peptide of claim 1, and a pharmaceutically acceptable excipient.

4. The pharmaceutical composition of claim 3, wherein the composition contains 0.00002 to 5% by weight of the peptide.

5. The pharmaceutical composition of claim 4, wherein the composition contains 0.00005 to 0.1% by weight of the peptide.

6. The pharmaceutical composition of claim 5, wherein the composition contains 0.0001 to 0.001% by weight of the peptide.

7. The pharmaceutical composition of claim 3, further comprising at least one other dermatologically active ingredient.

8. The pharmaceutical composition of claim 3, in the form of a cream, a milk, an oil-in-water emulsion, a water-in-oil emulsion, a multiple emulsion, a solution, a suspension, an aqueous gel, an oily gel, a hydroalcoholic gel, a lotion, a stick or a powder.

9. A method for reinforcing the dermo-epidermal junction, cell-cell adhesion and/or cell matrix adhesion in the epidermis and enhancing epidermal repair, the method comprising the application to the skin of an individual of an effective amount of a peptide of claim 1, wherein said amount is

```
                       SEQUENCE LISTING

<160> NUMBER OF SEQ ID NOS: 3

<210> SEQ ID NO 1
<211> LENGTH: 12
<212> TYPE: PRT
<213> ORGANISM: Human laminin 5

<400> SEQUENCE: 1

Thr Ala Leu Arg Ile Arg Ala Thr Tyr Gly Glu Tyr
  1               5                  10

<210> SEQ ID NO 2
<211> LENGTH: 12
<212> TYPE: PRT
<213> ORGANISM: Human laminin 5

<400> SEQUENCE: 2

Gly Leu Thr Lys Thr Tyr Thr Phe Arg Leu Asn Glu
  1               5                  10

<210> SEQ ID NO 3
<211> LENGTH: 12
<212> TYPE: PRT
<213> ORGANISM: Human laminin 5

<400> SEQUENCE: 3

Asp Val Lys Asn Leu Glu Asn Ile Arg Asp Asn Leu
  1               5                  10
``` effective for reinforcing the dermo-epidermal junction, cell-cell adhesion and/or cell matrix adhesion in the epidermis and enhancing epidermal repair.

10. The method of claim 9 for treating a skin impairment caused by a dermatological disorder.

11. The method of claim 9 for treating a skin impairment in which skin is made fragile by cosmetic or therapeutic treatment.

12. The method of claim 9 for the treatment or prevention of skin aging.

13. A cosmetic composition for the treatment of skin comprising the peptide of claim 1 and a cosmetically active ingredient.

14. The cosmetic composition of claim 13, wherein said composition contains 0.00002 to 5%, by weight of the peptide.

15. The cosmetic composition of claim 14, wherein said composition contains 0.00005 to 0.1% by weight of the peptide.

16. The cosmetic composition of claim 14, wherein said composition contains 0.0001 to 0.001% by weight of the peptide.

17. The cosmetic composition of claim 13, wherein said composition is in the form of a cream, a milk, an oil-in-water emulsion, a water-in-oil emulsion, a multiple emulsion, a solution, a suspension, an aqueous gel, an oily gel, a hydroalcoholic gel, a lotion, a stick or a powder.

18. A method of cosmetic treatment of skin wherein the cosmetic composition of claim 13 is applied to the skin of an individual; wherein said application of said cosmetic composition is effective for cosmetic treatment of the skin of said individual.

19. The method of claim 12, wherein the skin aging is wrinkles, loose skin, loss of elasticity, slower healing, senile xerosis, changes to the skin's pigmentation system, reduced skin vascularisation and changes to skin appendages.

20. The method of claim 19, wherein the skin appendages are nails.

* * * * *